United States Patent
Aimone et al.

(10) Patent No.: US 12,251,236 B2
(45) Date of Patent: Mar. 18, 2025

(54) WEARABLE COMPUTING DEVICE

(71) Applicant: INTERAXON INC., Toronto (CA)

(72) Inventors: Christopher Allen Aimone, Toronto (CA); Samuel Thomas MacKenzie, Toronto (CA); Amanda Fleury, Toronto (CA); Marta Zacharowska, Toronto (CA); Graeme Moffat, Toronto (CA)

(73) Assignee: INTERAXON INC., Toronto (CA)

( * ) Notice: Subject to any disclaimer, the term of this patent is extended or adjusted under 35 U.S.C. 154(b) by 334 days.

(21) Appl. No.: 16/206,488

(22) Filed: Nov. 30, 2018

(65) Prior Publication Data

US 2019/0200925 A1 Jul. 4, 2019

Related U.S. Application Data

(60) Provisional application No. 62/643,007, filed on Mar. 14, 2018, provisional application No. 62/613,492, filed on Jan. 4, 2018.

(51) Int. Cl.
*A61B 5/00* (2006.01)
*A61B 5/0205* (2006.01)
(Continued)

(52) U.S. Cl.
CPC .......... *A61B 5/6803* (2013.01); *A61B 5/0205* (2013.01); *A61B 5/24* (2021.01);
(Continued)

(58) Field of Classification Search
None
See application file for complete search history.

(56) References Cited

U.S. PATENT DOCUMENTS 5,983,129 A * 11/1999 Cowan ................. A61B 5/378
600/544
9,579,060 B1 * 2/2017 Lisy .................... A42B 3/0453
(Continued)

FOREIGN PATENT DOCUMENTS

EP 2448477 B1 10/2014
JP 2011502647 A 1/2017
(Continued)

OTHER PUBLICATIONS

WIPO, International Search Report and Written Opinion for PCT Application No. PCT/CA2018/051536 dated Feb. 12, 2019.
(Continued)

*Primary Examiner* — Aurelie H Tu
(74) *Attorney, Agent, or Firm* — Norton Rose Fulbright Canada LLP

(57) ABSTRACT

A wearable device to wear on a head of a user includes a flexible band generally shaped to correspond to the user's head, the band having at least a front portion to contact at least part of a frontal region of the user's head, a rear portion to contact at least part of an occipital region of the user's head, and at least one side portion extending between the front portion and the rear portion to contact at least part of an auricular region of the user's head. A deformable earpiece is connected to the at least one side portion, the deformable earpiece including conductive material to provide at least one bio-signal sensor to contact at least part of the auricular region of the user's head. At least one additional bio-signal sensor is disposed on the band to receive bio-signals from the user.

23 Claims, 35 Drawing Sheets

(51) Int. Cl.
*A61B 5/24* (2021.01)
*G06F 3/01* (2006.01)
*A61B 5/024* (2006.01)
*A61B 5/1455* (2006.01)

(52) U.S. Cl.
CPC ............ *A61B 5/7405* (2013.01); *G06F 3/015* (2013.01); *A61B 5/02416* (2013.01); *A61B 5/14551* (2013.01); *A61B 5/6817* (2013.01); *A61B 2562/0219* (2013.01); *A61B 2562/0223* (2013.01)

(56) References Cited

U.S. PATENT DOCUMENTS

| | | | |
|---|---|---|---|
| 2005/0043652 A1* | 2/2005 | Lovett | A61B 5/4812 600/595 |
| 2007/0112277 A1* | 5/2007 | Fischer | A61B 5/6817 600/544 |
| 2008/0165017 A1* | 7/2008 | Schwartz | A61B 5/486 600/324 |
| 2008/0177197 A1 | 7/2008 | Lee et al. | |
| 2009/0018427 A1* | 1/2009 | Causevic | A61B 5/38 600/383 |
| 2013/0303837 A1* | 11/2013 | Berka | A61B 5/369 600/28 |
| 2014/0347265 A1 | 11/2014 | Aimone et al. | |
| 2015/0000006 A1 | 1/2015 | Anderson | |
| 2016/0077547 A1* | 3/2016 | Aimone | A61B 5/0022 345/8 |
| 2016/0158486 A1 | 6/2016 | Colbaugh et al. | |
| 2016/0270656 A1* | 9/2016 | Samec | A61B 3/024 |
| 2016/0345901 A1* | 12/2016 | Connor | G16H 40/63 |
| 2016/0367189 A1* | 12/2016 | Aimone | A61B 5/291 |
| 2017/0042439 A1* | 2/2017 | Yeow | A61B 5/165 |
| 2017/0112406 A1* | 4/2017 | Li | A61B 5/16 |
| 2017/0296121 A1* | 10/2017 | Dar | A61N 1/0484 |
| 2018/0368717 A1* | 12/2018 | Soulet De Brugiere | H04B 11/00 |

FOREIGN PATENT DOCUMENTS

| | | |
|---|---|---|
| JP | 2017086543 A | 5/2017 |
| WO | 2012170816 A2 | 12/2012 |
| WO | 2015100499 A1 | 7/2015 |
| WO | 2016119665 A1 | 8/2016 |

OTHER PUBLICATIONS

European Patent Office, Extended European Search Report dated Oct. 18, 2021 for European Patent Application No. 18898031.2.

Chinese National Intellectual Property Administration (CNIPA), Office Action dated Apr. 27, 2022 for Chinese Patent Application No. 201880007500.4.

Chinese National Intellectual Property Administration (CNIPA), Office Action dated Jul. 28, 2021 for Chinese Patent Application No. 201880007500.4.

Japan Patent Office, Notification of Reasons for Refusal dated Oct. 4, 2022 for Japanese Patent Application No. 2020-536946.

Japan Patent Office, Notification of Reasons for Refusal dated Mar. 28, 2023 for Japanese Patent Application No. 2020-536946.

* cited by examiner

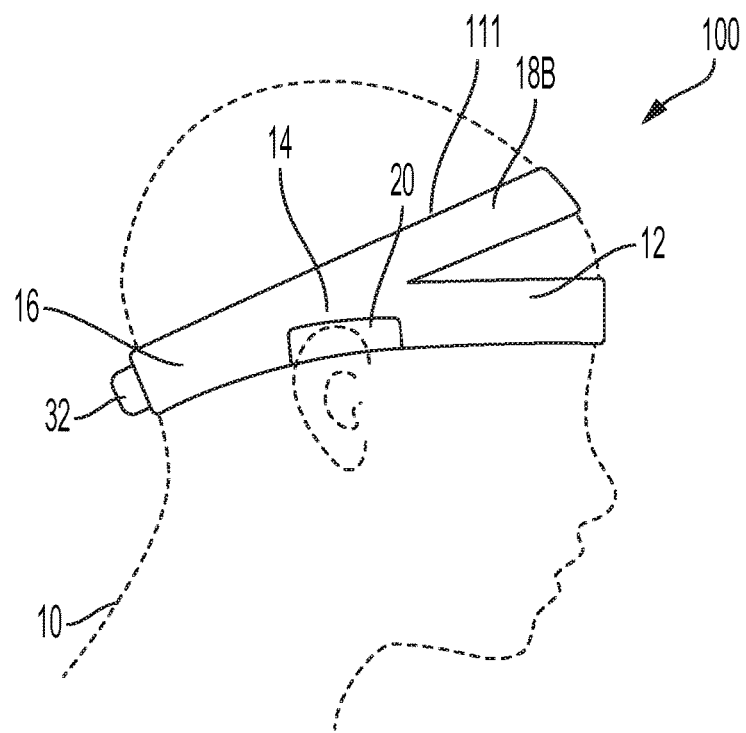
FIG. 5
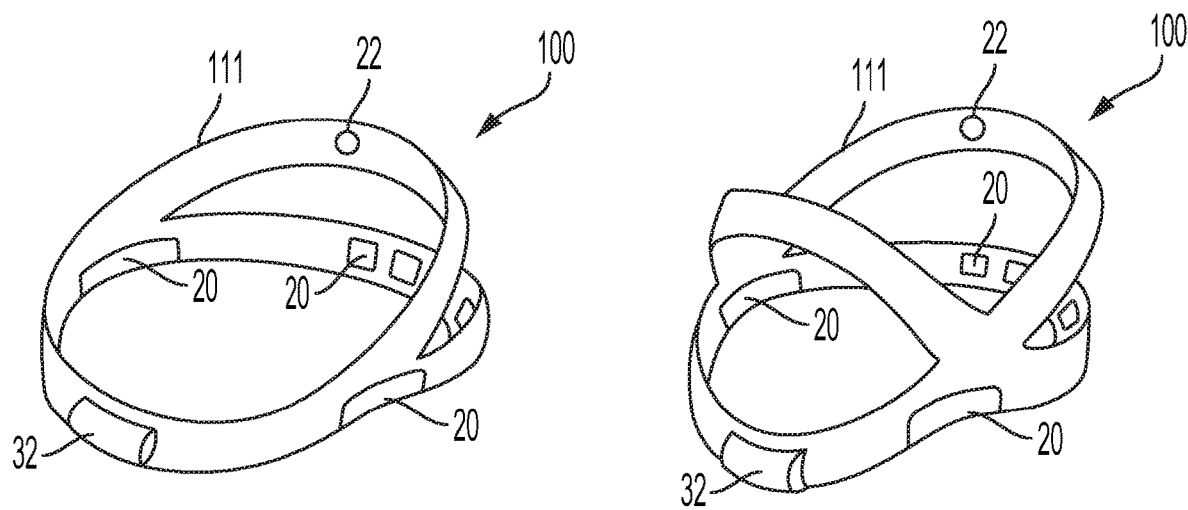
FIG. 6          FIG. 7

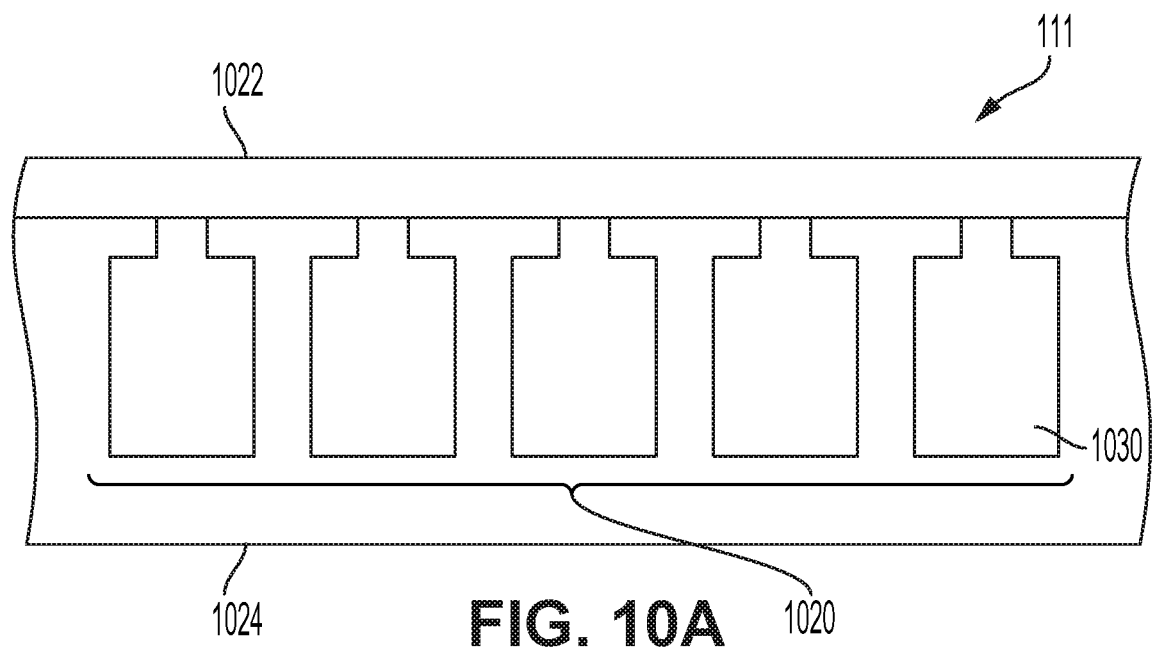
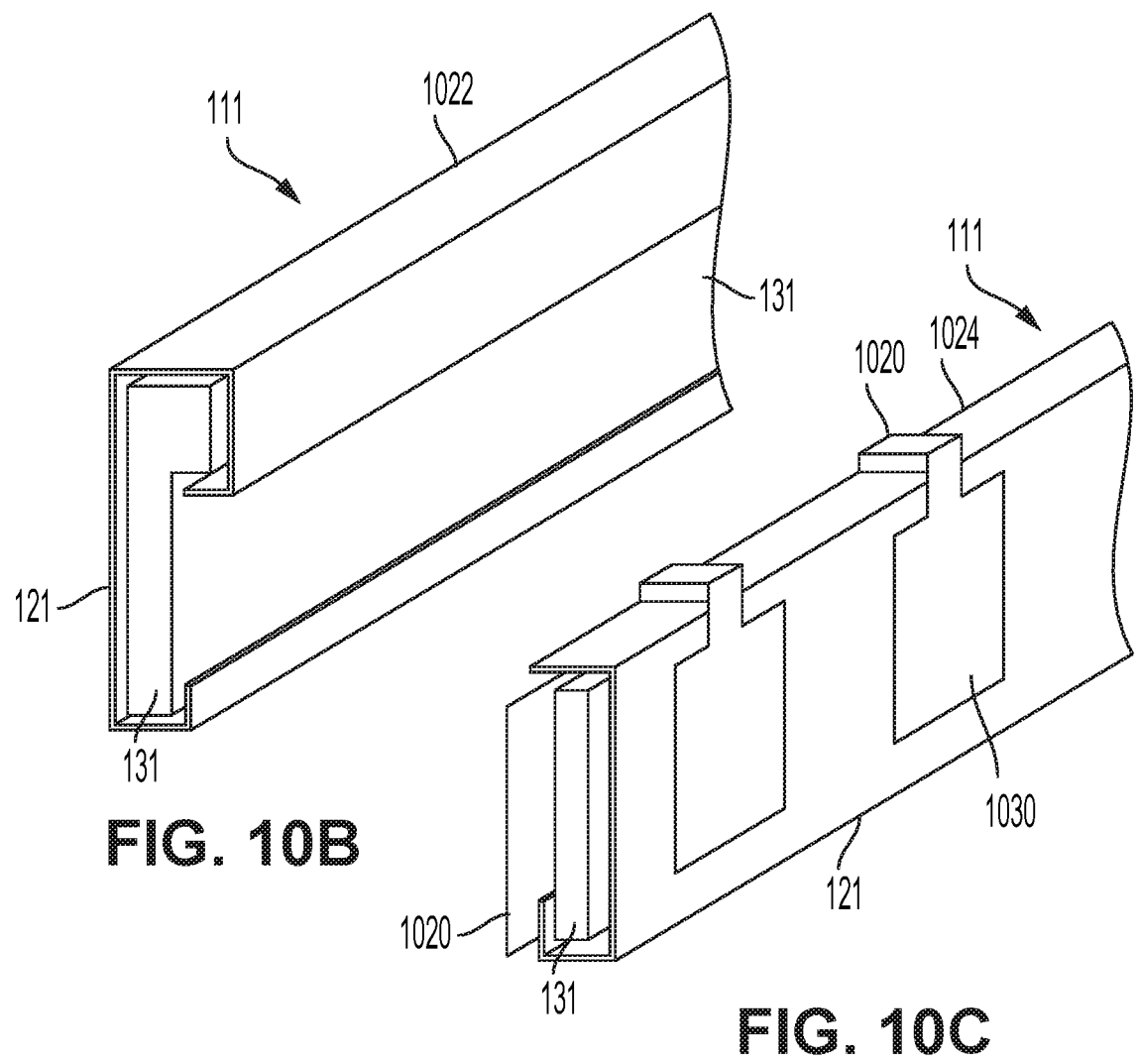

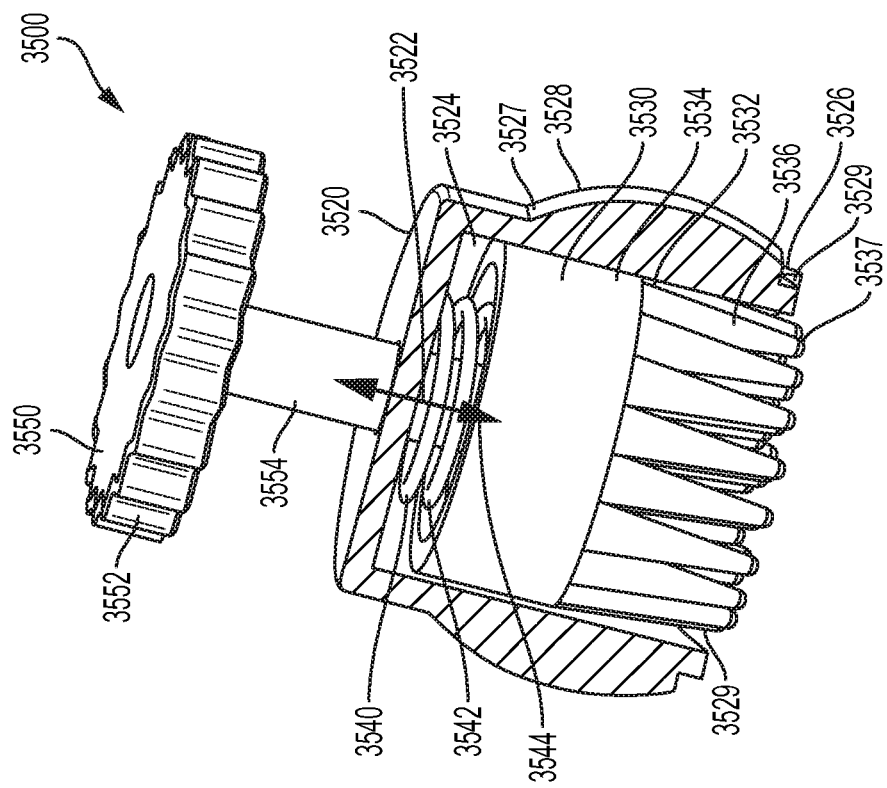
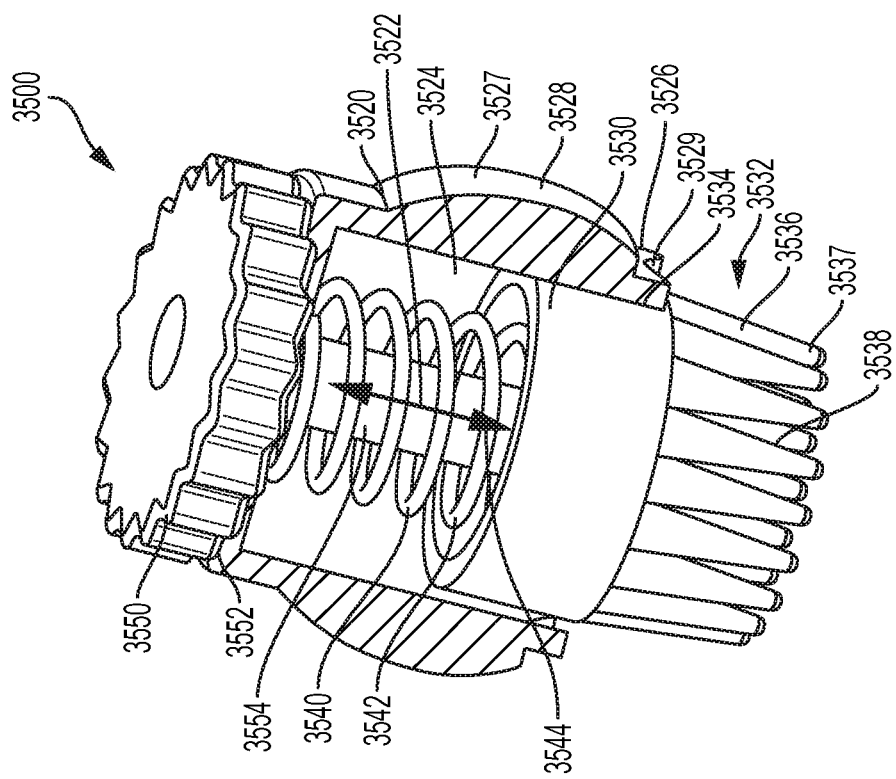

WEARABLE COMPUTING DEVICE

CROSS-REFERENCE TO RELATED APPLICATIONS

This application claims priority from U.S. Provisional Patent Application No. 62/643,007 filed on Mar. 14, 2018 and U.S. Provisional Patent Application No. 62/613,492 filed on Jan. 4, 2018, the contents of which are hereby incorporated by reference.

FIELD

The present disclosure relates to wearable devices. More specifically, the present disclosure relates to wearable devices with brainwave sensing components and that can be worn on the head of a user.

BACKGROUND

A user may interact with a computing device for example using a keyboard, mouse, track pad, touch screen, or motion-capture devices. As the ways in which humans interact with computing devices change, computers may become usable for new purposes, or more efficient in performing existing tasks. A user command to a computing device that may require several commands on a keyboard may be instead associated with a thought or gesture captured and processed by a sensory input device. As the human body has many parts which may be controlled through voluntary movement, there are opportunities for capturing and interpreting other movements for interacting with a computing device.

Bio-signals are signals that are generated by biological beings that can be measured and monitored. Electroencephalographs, galvanometers, and electrocardiographs are examples of devices that are used to measure and monitor bio-signals generated by humans.

A human brain generates bio-signals such as electrical patterns, which may be measured/monitored using an electroencephalogram ("EEG"). These electrical patterns, or brainwaves, are measurable by devices such as an EEG. Typically, an EEG will measure brainwaves in an analog form. Then, these brainwaves may be analyzed either in their original analog form or in a digital form after an analog to digital conversion.

Measuring and analyzing bio-signals such as brainwave patterns can have a variety of practical applications. For example, brain computer interfaces ("BCI") have been developed that allow users to control devices and computers using brainwave signals. In another example, analysis of brainwave patterns during sleep may allow users to understand their sleep patterns and/or improve their quality of sleep.

In order to obtain bio-signal data, it may be desirable for sensors to be in constant contact with the user. Accordingly, it may be desirable to provide comfortable wearable devices, especially if the device is worn for extended periods, such as overnight, in the case of sleep monitoring; or during periods of high activity or movement.

SUMMARY

According to an aspect, there is provided a wearable device to wear on a head of a user, the device comprising: a flexible band generally shaped to correspond to the user's head, the band having at least a front portion to contact at least part of a frontal region of the user's head, a rear portion to contact at least part of an occipital region of the user's head, and at least one side portion extending between the front portion and the rear portion to contact at least part of an auricular region of the user's head; a deformable earpiece connected to the at least one side portion, the deformable earpiece comprising conductive material to provide at least one bio-signal sensor to contact at least part of the auricular region of the user's head; and at least one additional bio-signal sensor disposed on the band to receive bio-signals from the user.

In some embodiments, the deformable earpiece is to contact at least part of an ear of the user.

In some embodiments, the deformable earpiece is to contact at least part of a mastoid bone region of the user.

In some embodiments, the deformable earpiece is generally curved.

In some embodiments, the deformable earpiece defines a shape of a generally semicircular perimeter.

In some embodiments, the conductive material is a conductive rubber.

In some embodiments, the at least one bio-signal sensor is an electrophysiological sensor.

In some embodiments, the at least one side portion comprises a right side portion extending between the front portion and the rear portion and a left side portion extending between the front portion and the rear portion.

In some embodiments, the at least one additional bio-signal sensor is disposed on at least one of the front portion and the rear portion.

In some embodiments, the at least one additional bio-signal sensor is an electrophysiological sensor.

In some embodiments, the front portion and the rear portion are joined at the at least one side portion at an oblique angle.

In some embodiments, the band comprises a deformable soft fabric.

In some embodiments, the band comprises at least one of a woven fabric, a knit fabric, and a non-woven fabric.

In some embodiments, the band comprises an elastic substrate.

In some embodiments, the at least one additional bio-signal sensor comprises a conductive material located at an inward face of the substrate, for receiving bio-signals from the user, and extending through apertures of the elastic substrate to an outward face of the substrate.

In some embodiments, the at least one additional bio-signal sensor comprises a flexible printed circuit, a film, or a combination thereof.

In some embodiments, the film comprises a conductive elastomer, a conductive urethane, or other conductive film.

In some embodiments, the wearable device further comprises an electronics module connected to the at least one bio-signal sensor to receive bio-signals from the at least one bio-signal sensor.

In some embodiments, the electronics module is selectively mountable to the band.

In some embodiments, the electronics module is disposed on the band and selectively removable from the band In some embodiments, the electronics module is disposed on the band at at least one of the front portion and the rear portion.

In some embodiments, the electronics module comprises a power supply and a computer system.

In some embodiments, the wearable device further comprises at least one overhead support strap joined to the loop.

In some embodiments, the at least one overhead support strap includes a crown strap for contacting at least part of a crown of the user's head, a top strap for contacting at least part of a top of the user's head, or any combination thereof.

In some embodiments, the wearable device further comprises a hair-penetrating sensor disposed on the at least one overhead support strap.

In some embodiments, the wearable device further comprises an auxiliary sensor selected from an optical heart rate sensor, a pulse oximeter sensor, a gyroscope, an accelerometer, a magnetometer, or any combination thereof.

In some embodiments, the auxiliary sensor is disposed on the loop to contact the forehead or a temple of the user's head.

In some embodiments, the at least one additional bio-signal sensor comprises an inner-ear sensor to contact an ear canal of the user.

In some embodiments, the wearable device further comprises a speaker disposed at a distance from the inner-ear sensor.

In an aspect, embodiments described herein provide a wearable device including a forehead contacting portion; two ear contacting portions; and an occipital contacting portion. The forehead contacting portion, the two ear contacting portions, and the occipital contacting portion are joined together as a loop such that, when worn, the two ear contact portions contact the tops of a user's ears and the occipital contacting portion contacts the bottom of the user's occipital bone. The device further includes at least one bio-signal sensor located on the loop for receiving bio-signals from the user.

According to another aspect, there is provided a bio-signal sensor including a body, an electrode extendable into the body, the electrode having a contact end configured to receive an electrical bio-signal from a user's skin, wherein in response to a downward force acting on the bio-signal sensor to urge the bio-signal sensor against the user's skin and upon contact with the user's skin, the electrode is configured for movement into the body along a movement axis, an actuator attached to the body and operatively connected to the electrode urging the electrode out of the body along the movement axis toward an extended position, wherein in the absence of the downward force, the electrode is disposed in the extended position, and a contact adjuster connected to the electrode, the contact adjuster includes a handle manipulatable by the user to reduce noise of the electrical bio-signal caused by impedance of the user's hair Other features will become apparent from the drawings in conjunction with the following description.

In this respect, before explaining any embodiments described herein in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF DRAWINGS

Embodiments will now be described, by way of example only, with reference to the attached figures.

FIG. 5 illustrates a side view of an embodiment of the wearable device having a top strap when worn by a user.

FIG. 6 illustrates a perspective view of an embodiment of the wearable device having a top strap and a hair-penetrating sensor.

FIG. 7 illustrates a perspective view of an embodiment of the wearable device having a top strap, a crown strap, and a hair-penetrating sensor.

FIG. 10A is a rear view of an outer layer and an inner layer of a wearable device having a flexible printed circuit board, according to an embodiment.

FIG. 10B is a perspective view of the outer layer of FIG. 10A.

FIG. 10C is a perspective view of the inner layer and the flexible printed circuit board of FIG. 10A.

FIG. 20 illustrates a partial cross-sectional view of a through-hair bio-signal sensor in an uncompressed state, according to an embodiment.

FIG. 21 illustrates a partial cross-sectional view of the bio-signal sensor of FIG. 20 in a compressed state.

DETAILED DESCRIPTION

Figure 1:
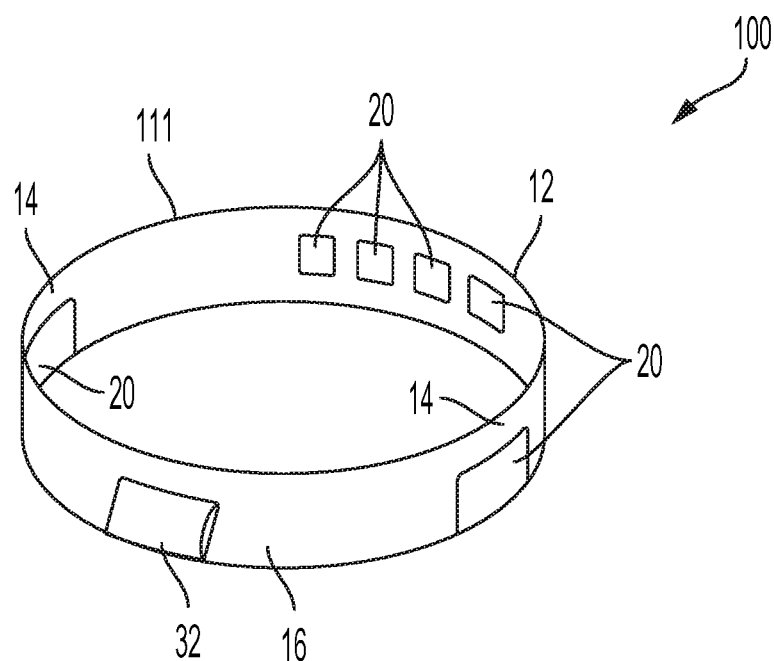
FIG. 1 illustrates a perspective view of an embodiment of a wearable device.

As used herein, the terms "downward" or "inward" generally refer to a direction toward a user's skin. Similarly, "lower" indicates a component disposed downward relative to another component. In contrast "upward", "upper", or "outward" are generally in a direction opposite the "downward" or "lower" component.

In an aspect, a computer system is provided that is implemented by one or more computing devices. The computing devices may include one or more client or server computers in communication with one another over a near-field, local, wireless, wired, or wide-area computer network, such as the Internet, and at least one of the computers is configured to receive signals from sensors worn by a user.

In an implementation, the sensors include one more bio-signal sensors, such as electroencephalogram (EEG) sensors, electromyography (EMG) sensors, galvanometer sensors, electrocardiograph sensors, heart rate sensors such as photoplethysmography (PPG), eye-tracking sensors, blood pressure sensors, breathing sensors, pedometers, gyroscopes, and any other type of sensor. The sensors may be of various types, including: electrical bio-signal sensor in electrical contact with the user's skin; capacitive bio-signal sensor in capacitive contact with the user's skin; blood flow sensor measuring properties of the user's blood flow; and wireless communication sensor placed sub-dermally underneath the user's skin. Other sensor types may be possible.

The sensors may be connected to a wearable device, which may be a wearable computing device or a wearable sensing device such as a wearable headset or headband computer worn by the user. The sensors may be connected to the headset by wires or wirelessly. The headset may further be in communication with another computing device, such as a laptop, tablet, or mobile phone such that data sensed by the headset through the sensors may be communicated to the other computing device for processing at the computing device, or at one or more computer servers, or as input to the other computing device or to another computing device. The one or more computer servers may include local, remote, cloud based or software as a service platform (SAAS) servers.

Embodiments of the system may provide for the collection, analysis, and association of particular bio-signal and non-bio-signal data with specific mental states for both individual users and user groups. The collected data, analyzed data or functionality of the systems and methods may be shared with others, such as third party applications and other users. Connections between any of the computing devices, internal sensors (contained within the wearable device), external sensors (contained outside the wearable device), user effectors, and any servers may be encrypted. Collected and analyzed data may be used to build a user profile that is specific to a user. The user profile data may be analyzed, such as by machine learning processes, either individually or in the aggregate to function as a BCI, or to improve the algorithms used in the analysis. Optionally, the data, analyzed results, and functionality associated with the system can be shared with third party applications and other organizations through an API. One or more user effectors may also be provided at the wearable device or other local computing device for providing feedback to the user, for example, to vibrate or provide some audio or visual indication to assist the user in achieving a particular mental state, such as a meditative state.

The wearable device may include a camera, a display, and bio-signal measuring means to sample a user's environment as well as the user's bio-signals, determining the user's state and context through sensors and user input. The wearable device may include at least one user-facing camera to track eye movement. In a particular aspect of the invention, the wearable device may be in a form resembling eyeglasses wearable on the user's face. Optionally, at least one camera may be oriented to generally align with the user's field of view.

In another aspect, the wearable device may be in a form of at least one sensor adapted to being placed at or adhered to the user's head or face. Each sensor may optionally communicate with one another either through wires or wirelessly. Each sensor may optionally communicate with a controller device either through wires or wirelessly. The controller device may be mounted to the wearable device in order to reside at or near the user's head or face. Alternatively, the controller device may be located elsewhere on the user's body, such as in a bag or pocket of the user's clothing. The controller device may also be disposed somewhere outside the user's body. For example, the sensors may monitor the user, storing data in local storage mounted to the wearable device, and once moving into proximity with the controller device, the sensors, or a transmitter of the wearable device may transmit stored data to the controller device for processing. In this implementation, the wearable device would be predominantly usable by the user when located nearby the controller device.

The wearable device may include a camera, a display and bio-signal measuring means. At least one of the bio-signal measuring means may employ at least one sensor in order to measure brain activity. Brain activity may be measured through electroencephalography ("EEG") techniques electrically, or through functional near-infrared spectroscopy ("MIR") techniques measuring relative changes in hemoglobin concentration through the use of near infrared light attenuation. A sensor employing pulse oximetry techniques may also be employed in the wearable device. Optionally, the wearable device may include at least one sensor measuring eye activity using electrooculography ("EOG") techniques. Other sensors tracking other types of eye movement may also be employed.

In various implementations, the wearable device may include a variety of other sensors and input means. For example, the wearable device may comprise at least one audio transducer such as a single microphone, a microphone array, a speaker, and headphones. The wearable device may comprise at least one inertial sensor for measuring movement of the wearable device. The wearable device may comprise at least one touch sensor for receiving touch input from the user.

The wearable device may sample from both the user's environment and bio-signals simultaneously or generally contemporaneously to produce sampled data. The sampled data may be analyzed by the wearable device in real-time or at a future predetermined time when not being worn by the user.

The wearable device may comprise user input detection methods that are adaptive and improve with use over time. Where the user attempts to command the wearable device, and the wearable device responds in an unexpected way, the user may attempt to correct the previous input by indicating that the wearable device response was incorrect, and retrying the initial command again. Over time, the wearable device may refine its understanding of particular user inputs that are corrected. Some user inputs may be easier to successfully measure with a high degree of accuracy than others. It may be preferable to assign a high-accuracy input to command the wearable device that the previous input was incorrect. For example, tapping the wearable device in a particular spot may indicate that the previous input response was incorrect. Explicit training such as with voice recognition may also be used to configure and command the wearable device.

Optionally, the wearable device may itself only provide bio-signal sensors and a processor for processing measurements from the sensors. The wearable device may communicate these measurements or data derived from processing the measurements to one or more secondary devices, such as glasses with video cameras embedded therein. In any of the implementations, embodiments, or applications discussed herein, it should be understood that some actions may be carried out by a plurality of interconnected devices, or just one of the wearable devices of the present invention. For example, the wearable device may not include a display. In such an example, the wearable device may communicate visual information to the user through the use of a second device, such as glasses with video cameras embedded therein, which does include a display.

Sensors usable with the wearable device may come in various shapes and be made of various materials. For example, the sensors may be made of a conductive material, including a conductive composite like rubber or conductive metal. The sensors may also be made of metal plated or coated materials such as stainless steel, silver-silver chloride, and other materials.

In addition to or instead of processing bio-signal measurements on the wearable device, the wearable device may communicate with one or more computing devices in order to distribute, enhance, or offload the processing of the bio-signal measurements taken or received by the wearable device. In particular, the one or more computing devices may maintain or have access to one or more databases maintaining bio-signal processing data, instructions, algorithms, associations, or any other information which may be used or leveraged in the processing of the bio-signal measurements obtained by the wearable device. The computing devices may include one or more client or server computers in communication with one another over a near-field, local, wireless, wired, or wide-area computer network, such as the Internet, and at least one of the computers may be configured to receive signals from sensors of the wearable device.

The wearable device may further be in communication with another computing device, such as a laptop, tablet, or mobile phone such that data sensed by the headset through the sensors may be communicated to the other computing device for processing at the computing device, or at one or more computer servers, or as input to the other computing device or to another computing device. The one or more computer servers may include local, remote, cloud based or software as a service platform (SAAS) servers. Embodiments of the system may provide for the collection, analysis, and association of particular bio-signal and non-bio-signal data with specific mental states for both individual users and user groups. The collected data, analyzed data or functionality of the systems and methods may be shared with others, such as third party applications and other users. Connections between any of the computing devices, internal sensors (contained within the wearable device), external sensors (contained outside the wearable device), user effectors (components used to trigger a user response), and any servers may be encrypted. Collected and analyzed data may be used to build a user profile that is specific to a user. The user profile data may be analyzed, such as by machine learning algorithms, either individually or in the aggregate to function as a BCI, or to improve the algorithms used in the analysis. Optionally, the data, analyzed results, and functionality associated with the system can be shared with third party applications and other organizations through an API. One or more user effectors may also be provided at the wearable device or other local computing device for providing feedback to the user, for example, to vibrate or provide some audio or visual indication to assist the user in achieving a particular mental state, such as a meditative state.

A cloud-based implementation for processing and analyzing the sensor data may provide one or more advantages including: openness, flexibility, and extendibility; manageable centrally; reliability; scalability; being optimized for computing resources; having an ability to aggregate information across a number of users; and ability to connect across a number of users and find matching sub-groups of interest. While embodiments and implementations of the present invention may be discussed in particular non-limiting examples with respect to use of the cloud to implement aspects of the system platform, a local server, a single remote server, a SAAS platform, or any other computing device may be used instead of the cloud.

In one implementation of the system, a Multi-modal EEG Data-Collection and Adaptive Signal Processing System (MED-CASP System) for enabling single or multi-user mobile brainwave applications may be provided for enabling BCI applications. This system platform may be implemented as a hardware and software solution that is comprised of an EEG headset such as the wearable device of the present invention, a client side application and a cloud service component. The client side application may be operating on a mobile or desktop computing device. The system may provide for: estimation of hemispheric asymmetries and thus facilitate measurements of emotional valence (e.g. positive vs. negative emotions); and better signal-t-noise ratio (SNR) for global measurements and thus improved access to high-beta and gamma bands, which may be particularly important for analyzing cognitive tasks such as memory, learning, and perception. It has also been found that gamma bands are an important neural correlate of meditation expertise.

In the same or another non-limiting exemplary implementation, possible MED-CASP system features may include: uploading brainwaves and associated sensor and application state data to the cloud from mobile application; downloading brainwave & associated data from the cloud; real-time brain-state classification to enable BCI in games or other applications; transmitting real-time brain-state data to other users when playing a game to enable multi-user games; sharing brainwave data with other users to enable asynchronous comparisons of results; sharing brainwave data to other organizations or third party applications and systems; and support of cloud based user profiles for storing personal information, settings and pipeline parameters that have been tuned to optimize a specific user's experience. In this way, usage of the system platform can be device independent.

Each time analysis or processing of user bio-signal data (such as brainwave data) is performed, an instance of aspects of the software implementing the analysis functionality of the present invention may be generated by the wearable device, initiated at either the device or the cloud, in order to analyze the user's private bio-signal data using particular analysis or processing parameters applied during the analysis or processing. For simplicity, such an instance may be referred to as an algorithm "pipeline". Each instance of the pipeline may have an associated pipeline identifier ("ID"). Each pipeline may be associated with a particular activity type, user, bio-signal type of a particular user, application, or any other system platform-related data. Each pipeline may maintain particular pipeline parameters determined to analyze the user's bio-signal data in a particular way, consistent either with previous analysis of the particular user's bio-signal data, consistent with previous analysis of one or more other user's bio-signal data, or consistent with updated data at the cloud server derived from new or updated scientific research pertaining to the analysis of bio-signal data. Pipelines and/or pipeline parameters may be saved for future use at the client computing device or at the cloud. When a new pipeline is created for the user, the wearable device or the cloud may provide a new algorithm pipeline ID to be associated with the new pipeline at the cloud and at the device.

Each person's brainwaves are different, therefore requiring slightly different tunings for each user. Each person's brain may also learn over time, requiring the system platform to change algorithm parameters over time in order to continue to analyze the person's brainwaves. New parameters may be calculated based on collected data, and may form part of a user's dynamic profile (which may be called bio-signal interaction profile). This profile may be stored in the cloud, allowing each user to maintain a single profile across multiple computing devices. Other features of the same or another non-limiting exemplary implementation may include: improving algorithms through machine learning applied to collected data either on-board the client device or on the server; saving EEG data along with application state to allow a machine learning algorithm to optimize the methods that transform the user's brainwaves into usable control signals; sharing brainwave data with other applications on mobile device through a cloud services web interface; sharing brainwave data with other applications running on client devices or other devices in the trusted network to provide for the user's brainwave data to control or effect other devices; integration of data from other devices and synchronization of events with brainwave data aid in context aware analysis as well as storage and future analysis; performing time locked stimulation and analysis to support stimulus entrainment event-related potential ("ERP") analysis; and data prioritization that maximizes the amount of useful information obtainable from an incomplete data download (i.e. data is transmitted in order of information salience). The core functionality of the MED-CASP system may be wrapped as an externally-usable library and API so that another developer may use the platform's features in the developer's application(s). The library may be a static library and API for Unity3D, iOS, Android, OSX, Windows, or any other operating system platform. The system platform may also be configured to use a pre-compiled algorithm supplied by a third party within the library, including the ability for a third party developer using the library, to use the developer's own algorithms with the library. The system platform may also support headsets from a variety of vendors; personal data security through encryption; and sharing of un-curated data (optionally using time-limited and fidelity limited access) though the sharing of encryption keys.

Figure 2:
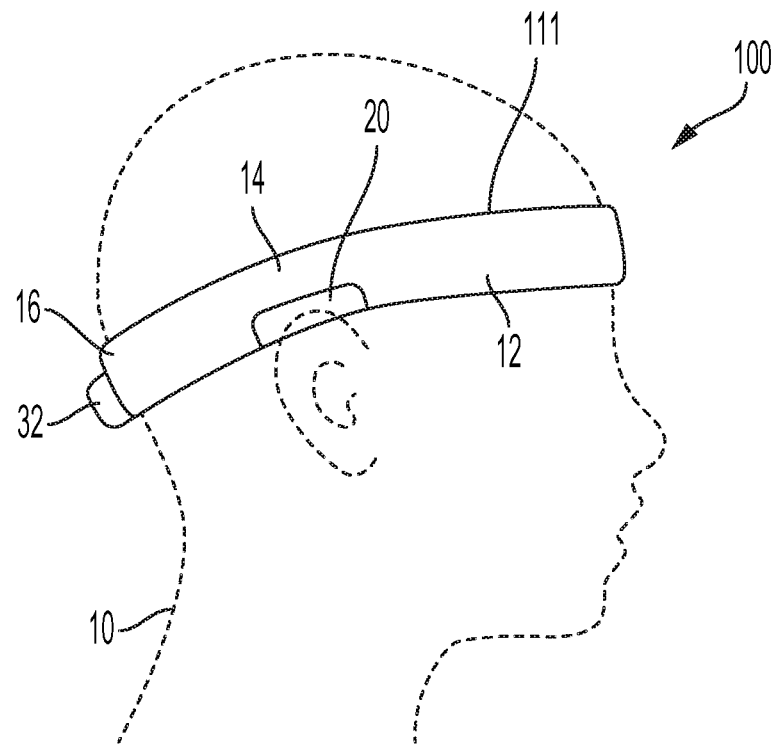
FIG. 2 illustrates a side view of the embodiment of the wearable device of FIG. 1 when worn by a user.

With reference to FIGS. 1 and 2, in an aspect of the present disclosure, a wearable device 100 includes a front portion (in an example, a forehead contacting portion 12), a rear portion (in an example, an occipital contacting portion 16) and at least one side portion—for example, a right side portion and a left side portion—(in an example, two ear contacting portions 14) extending between the front portion and the rear portion to contact at least part of an auricular region of the head of user 10. FIG. 2 illustrates a side view of a user 10 wearing a wearable device 100, according to an embodiment. The forehead contacting portion 12, the two ear contacting portions 14, and the occipital contacting portion 16 are joined to form a body 111, as a flexible band generally shaped to correspond to the head of user 10.

Body 111 may form, for example, in a loop configuration as shown in FIGS. 1 and 2 such that, when worn, the two ear contacting portions 14 contact the tops of a user's ears and the occipital contacting portion 16 contacts the bottom of the user's occipital bone. At least one bio-signal sensor 20 may be located on the loop and an inward facing side for receiving bio-signals from the user.

Body 111 may include fabric and elasticized portions. In some embodiments, some or all portions of body 111 are elastic or on an elastic substrate, while other portions or sections are relatively inelastic or rigid. Body 111 may be formed from a soft deformable fabric 121, for example, a woven, a knit, or a non-woven fabric. Fabric 121 may be formed, for example from a fabric that is cotton, synthetic, or any other suitable fabric. In some embodiments, fabric 121 of body 111 may be machine washable.

Body 111 may also include one or more reinforcing members 131 at various locations, for example to provide structural support to wearable device 100. Reinforcing members 131 may include a compressible foam, in an example, covered by a fabric, which may conform to the shape of the head of user 10. In some embodiments, the compressible foam may be formed of an open cell foam, such as a suitable open cell foam material. In some embodiments, the compressible foam may be formed of a closed cell foam, such as a neoprene. Compressible foam may be compressible such that when the wearable device 100 is affixed to the head of user 10, the compressible foam conforms to the head of user 10. In use, the compressible foam may be compressed and conform to the head of user 10 by clinching of body 111 to size and secure wearable device 100 to user 10. Wearable device 100 may be sized and secured to user 10, for example, using a cinch strap, fastened, for example, by hook and loop fasteners (such as Velcro™).

Body 111 may be formed from foam that is molded to a specific shape of a user's head. For example, the circumference of body 111 may taper to correspond to a head shape. Foam used in body 111 may be shaped, for example, heat-formed, to mold to a user's particular shape of head.

Other reinforcing materials, such as interfacing in an example, may be used to provide rigidity, inelasticity, and/or inflexibility in certain areas of body 111, for example, where components such as bio-signal sensor 20 may be mounted.

In some embodiments, shielding may be incorporated into the fabric of body 111, for example, to shield conductive lines between bio-signal sensors 20 and electronics module 32.

In some embodiments, the forehead contacting portion 12 and the occipital contacting portion 16 are arcuate and are joined by the two ear contacting portions 14. In some embodiments, the two arcuate portions are joined at each of the two ear contacting portions such that an angle forms between them, not as a straight line. In some embodiments, the angle is between about 90° and about 180°, between about 135° and about 180°, between about 155° and about 170°. In some embodiments, the angle is an oblique angle with the vertex located proximate the ear. A bend by the ear contacting portion 14 may allow a computing device to better conform to the head with less deformation of the wearable device 100 when worn and/or with better stability when worn. Further, a bend by the ear may follow the curvature of the ear, increasing the electrical contact area of a bio-signal sensor 20 located above the user's ear.

Contact with bio-signal sensors may be affected by barriers such as hair. Hair forms a physical barrier, lifting the bio-signal sensor away from the user's skin, especially if the hair is sufficiently dense that it forms a mat. As such, bio-signal sensors 20 may be placed on the device such that, when worn, the sensors are located on the head in an area with little hair. As such, in some embodiments, the at least one bio-signal sensor 20 is located on the forehead contacting portion 12, one or both of the two ear contacting portions 14, or any combination thereof. In some embodiments, the at least one bio-signal sensor 20 includes a bio-signal sensor located at each of the ear contacting portions. Bio-signal sensors 20 may be disposed in a fixed position on body 111. In some embodiments, bio-signal sensors 20 may be integrated into an aperture or track defined by body 111 that allows for lateral movement of bio-signal sensor 20 along body 111.

Bio-signal sensor 20 may be an electrophysiological sensor of various types, including: electrical bio-signal sensor in electrical contact with the user's skin; capacitive bio-signal sensor in capacitive contact with the user's skin; blood flow sensor measuring properties of the user's blood flow.

The locations of bio-signal sensors 20 on body 111 may be reinforced, for example with reinforcing member 131, to reduce flexibility or elasticity and increase rigidity of locations on body 111 in which bio-signal sensors 20 are disposed. In some embodiments, body 111 locations may be reinforced by using interfacing to reduce stretch of fabric 121 of body 111.

In an example, forehead contacting portion 12 may be reinforced to structurally support bio-signal sensors 20, while ear contacting portions 14 of body 111 may remain elastic.

In some embodiments, bio-signal sensor 20 may be formed from material including silver-painted vinyl, flexible printed circuit board ("PCB") with or without a conductive ink or precious metal plating such as silver or gold plating, conductive rubber such as heat-applied conductive rubber, conductive fabric (for example, silver ink on fabric), a conductive fabric laminate, and PEDOT-impregnated foam. Other suitable conductive materials may also be used.

Bio-signal sensors 20 may be integrated into body 111 in a configuration so as to allow body 111 to flex and be breathable. For example, a vinyl or plastic substrate with silver ink on it may be cut into a pattern such as repeating shapes (for example, repeating squares or hexagons, and applied to body 111.

Body 111 may also be reinforced, and made less flexible and more rigid, in regions in which bio-signal sensors 20 are mounted, so that bio-signal sensors 20 may move around less, in use.

Figure 8:
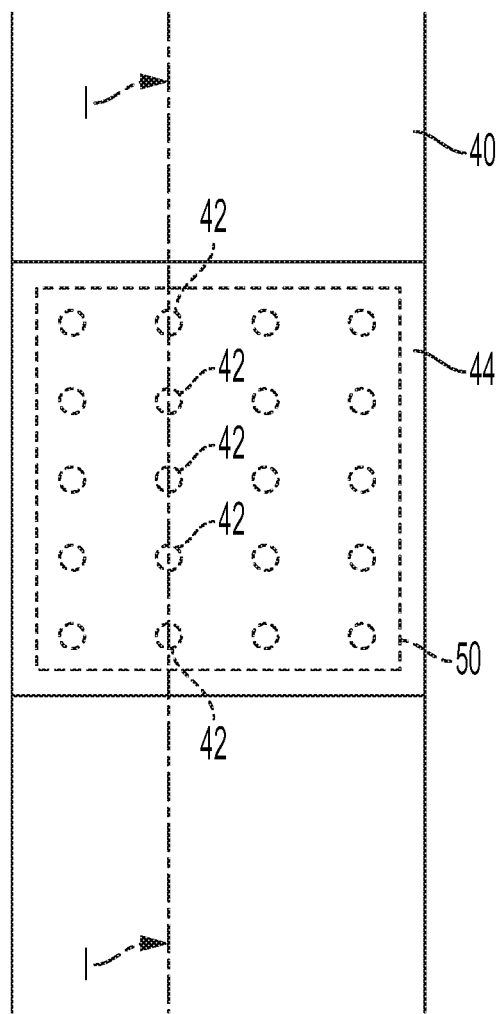
FIG. 8 is a top schematic view of a bio-signal sensor integrated into a fabric substrate according to an embodiment.
Figure 9:
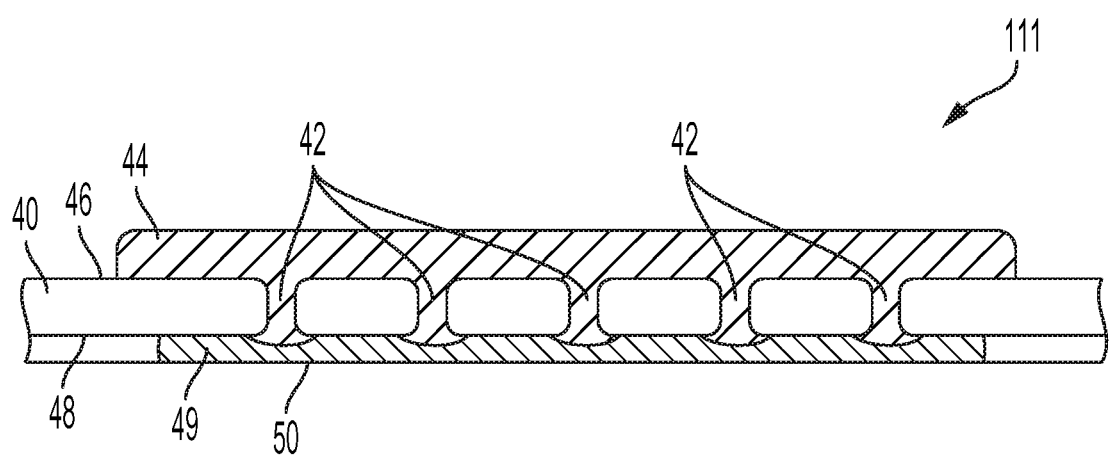
FIG. 9 is a cross-section schematic view of the bio-signal sensor integrated into the fabric substrate of FIG. 8 along lines I-I.

Having reference now to FIGS. 8 and 9, in some embodiments, body 111 or portions thereof include a substrate 40. FIG. 8 is a top schematic view of a bio-signal sensor integrated into a fabric substrate according to an embodiment. FIG. 9 is a cross-section schematic view of the bio-signal sensor integrated into the fabric substrate of FIG. 8 along lines I-I.

In some embodiments, substrate 40 is a woven or non-woven fabric substrate. In some embodiments, substrate 40 is an elastic material such as an elastic fabric. The elastic material may exhibit elastic deformation after being stretched to a length that is at least about 25%, 50%, 75%, 100%, 125% or 150% of the unstretched length. In an unstretched state, the loop may be slightly smaller than the circumference of the user's head. Once worn, the loop elongates to a stretched state around the user's head. In some embodiments, the loop is elongated from about 1% and about 50%, from about 5% to about 25%, or from about 5% to about 10% between the unstretched state and the stretched state. The tension exerted on the user's head and arising elastic forces due to the elongation of the loop tends to keep the device in place on the user's head.

A user may have an individual preference for levels of tension to keep the device in place on their head. As such, in some embodiments, the loop includes a tension adjuster. In some embodiments, the tension adjuster includes a buckle, for example, a sliding buckle near the back, a dial, hook and loop fasteners (such as Velcro™).

In some embodiments, a bio-signal sensor 20 is formed by applying a conductive layer 44 to the substrate 40. The conductive layer is applied to an inward face 46 of the substrate 40, the inward face 46 adapted to sit against the user's head when wearable device 10 is worn. In some embodiments, the conductive layer 44 is applied as a conductive ink. In some embodiments, the conductive ink includes silver, carbon, or combination thereof. In some embodiments, the conductive layer is applied by pad printing, silk screening, spraying, or painting. The conductive layer 44, when in contact with the user's skin, is able to receive electrical bio-signals from the user at the point of contact.

In some embodiments, the substrate defines a plurality of apertures 42 such that upon application of the conductive ink to the inward face 46 of the substrate 40, the ink flows through and coats the apertures 42, eventually flowing to an outward face 48 of the substrate 40. The ink coating the aperture 42 acts as a through-substrate via, providing a path for signals collected at the interface between the user and the conductive layer 44 at the inward face to be transmitted and collected at the outward face 48.

At the outward face 48, a signal collector 50 is electrically connected to the conductive layer 44, providing electrical connection between the conductive layer 44 of the bio-signal sensor to the electronics module 32. The placement of elements not at the inward face 46 reduces the presence of potentially uncomfortable stress points pressing on the user's skin, when worn. In some embodiments, the signal collector 50 is connected to the conductive layer 44 by a bonding layer 49 such as an adhesive layer or second conductive ink layer. In some embodiments, the signal collector 50 attached to the substrate, such as by stitching or welded (such as by RF welding) onto the substrate 40.

In some embodiments, the signal collector 50 includes a flexible printed circuit ("FPC") or a film 50. In some embodiments, the FPC includes a polyimide or similar film which is plated in copper and selectively removed (such as by etching) to create a circuit. The copper is optionally covered in another layer of polyimide or similar film or Liquid Solder mask. In some embodiments, the FPC includes a plurality of copper layers. In some embodiments, the FPC includes thicker polyimide or fiberglass or metal to provide stiffness to certain sections. In some embodiments, the film is a stretchable film, such as a thermoplastic elastomer, a thermoplastic urethane, or other plastic film. In some embodiments, the film may exhibit elastic deformation after having been stretched an elongation of at least 5%, 10%, 15%, 20%, 25%, 30%, 35%, 40%, 45%, or 50% as compared to its unstretched state.

In some embodiments, a covering layer is disposed over the substrate 40 and the signal collector 50. The covering layer may reduce protrusions that can catch on other surfaces, such as a pillow, helmet. In some embodiments, the covering layer is a fabric material, a rubber material, or any combination thereof.

As shown in FIGS. 10A to 10C, bio-signal sensor 20 may be formed from flexible printed circuit board ("PCB") 1020. PCB 1020 may have contacts 1030 on it formed from an appropriate conductive material such as silver ink. PCB 1020 may be configured on body 111 of wearable device 100 such that in use, contacts 1030 contact at least part of the forehead of user 10. Such a PCB may be hermetically sealed as long as the connections are appropriately sealed.

In some embodiments, body 111 may be formed of an outer layer 1022 and an inner layer 1024. Each of outer layer 1022 and inner layer 1024 may be formed from materials such as fabric 121 and reinforcing members 131 as described herein.

FIG. 10A is a rear view of outer layer 1022 and inner layer 1024 of body 111. FIG. 10B is a perspective view of outer layer 1022 of body 111. FIG. 10C is a perspective view of inner layer 1024 of body 111. As shown in FIG. 10C, PCB 1020 may fold over inner layer 1024.

Thus, as outer layer 1022 is affixed to inner layer 1024, the circuitry of PCB 1020 may be sandwiched between outer layer 1022 and inner layer 1024, while contacts 1030 remain exposed on inner layer 1024 to contact the forehead of user 10.

The use of two layers, namely outer layer 1022 and inner layer 1024, for example, in the configuration described herein, may protect the edges of PCB 1020 and protect circuitry of PCB 1020 (as encased between outer layer 1022 and inner layer 1024) and may provide reduced visible seams.

Figure 11:
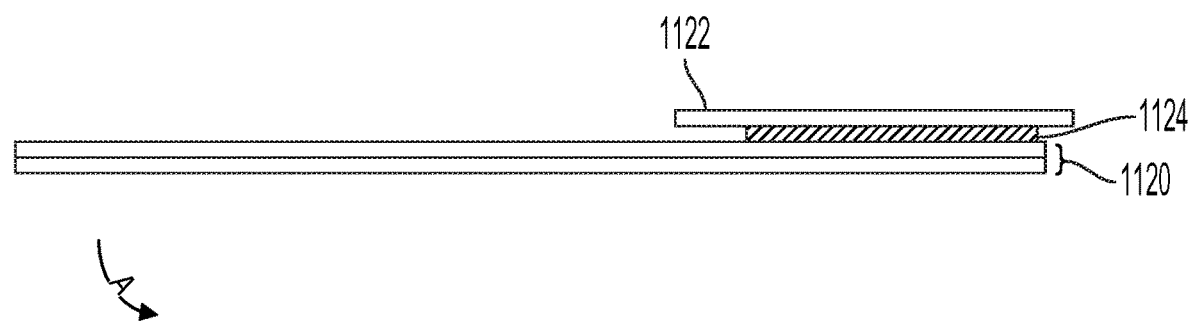
FIG. 11 is a side view of a flexible printed circuit board configuration, according to an embodiment.

FIG. 11 is a side view of a flexible printed circuit board configuration, according to an embodiment, which may be used as a bio-signal sensor 20 in wearable device 100. A flexible printed circuit board ("PCB") 1120 may be formed of copper and polyimide ("PI") arranged in PI-copper-PI layers.

API coverlay 1122 may be attached to PCB 1120 by way of adhesive layer 1124. In use, PI coverlay 1122 may be disposed in wearable device 100 to contact, for example, a forehead of user 10. PCB 1120 may thus be able to fold over in the direction shown by arrow A.

The configuration illustrated in FIG. 11 may allow for reduction of sharp edges and exposure of surfaces where tears may start in PCT 1120.

Figure 12A:
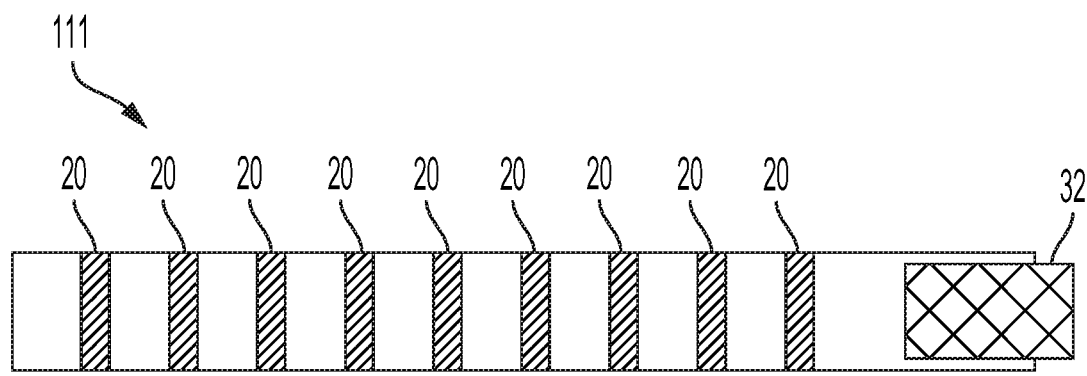
FIGS. 12A and 12B are schematic views of multiple bio-signal sensors disposed in a body of a wearable device, according to an embodiment.
Figure 12B:
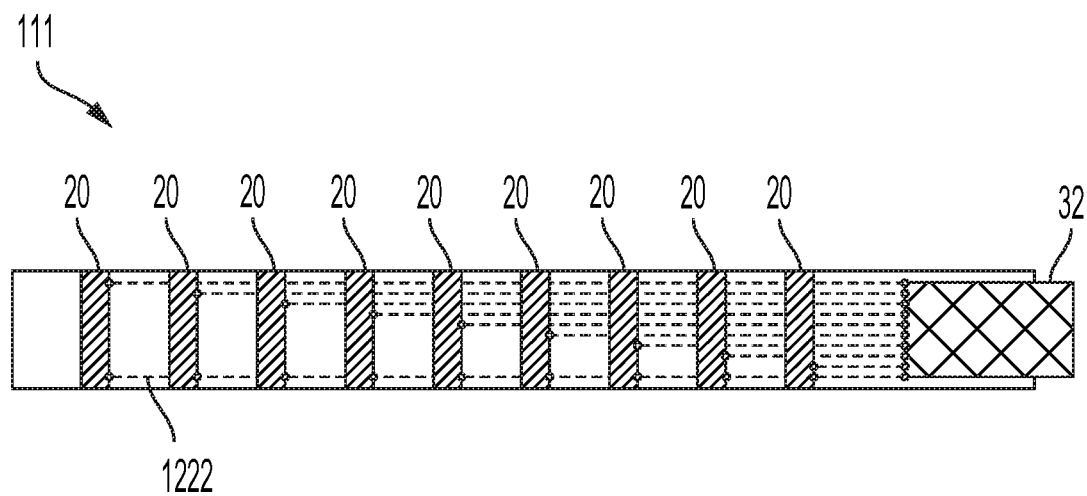

As shown in FIGS. 12A and 12B, multiple bio-signal sensors 20, such as electrodes, may be disposed in body 111 of wearable device 100.

FIGS. 12A and 12B illustrate an embodiment of wearable device 100 in which there is a redundant array of bio-signal sensor 20 electrodes connected to a single electronics module 32 by traces 1222. In an example, traces 1222 may be conductive thread. Electronics module 32 may use a signal quality indicator to assess which bio-signal sensor(s) 20 to use. For example, depending on where the received bio-signal is cleanest or strongest.

A bio-signal sensor 20 located and connected to an ear contacting portion 14 of wearable device 100 may be referred to as an "above-ear electrode", as described herein. Such an "above-ear electrode" may be a deformable earpiece that takes the form of an open bow-string above-ear electrode 1002, a closed bow-string above-ear electrode 1004, a shaped above-ear electrode 1102, and a moveable above-ear electrode 1202 as described below with reference to FIGS. 13A-13C, 14 and 15A-15B. Such above-ear electrodes may be configured to contact at least part of the auricular region of the user's head, for example, an ear or a mastoid bone region of user 10. The above-ear electrode may include a depressible area with a thin rubber cushion, air cushion, or gel cushion that can depress against an ear.

Figure 13B:
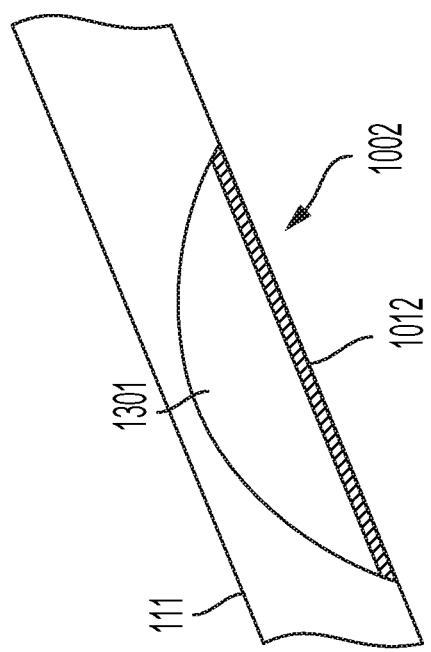
FIG. 13B is an expanded view thereof, according to an embodiment.
Figure 13C:
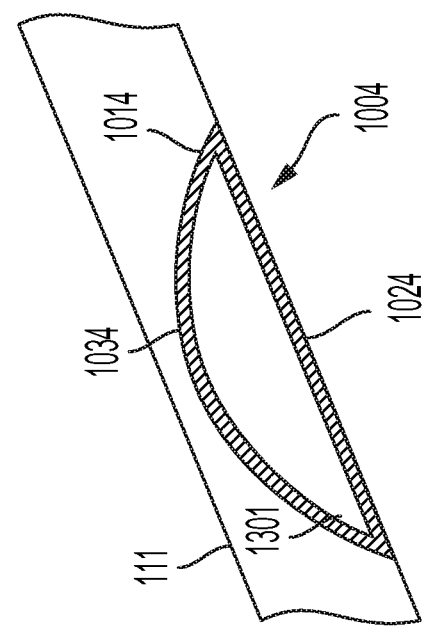
FIG. 13C illustrates an expanded schematic side view of an embodiment of a wearable device having an above-ear electrode a closed 'bow string' design, according to an embodiment.
Figure 13A:
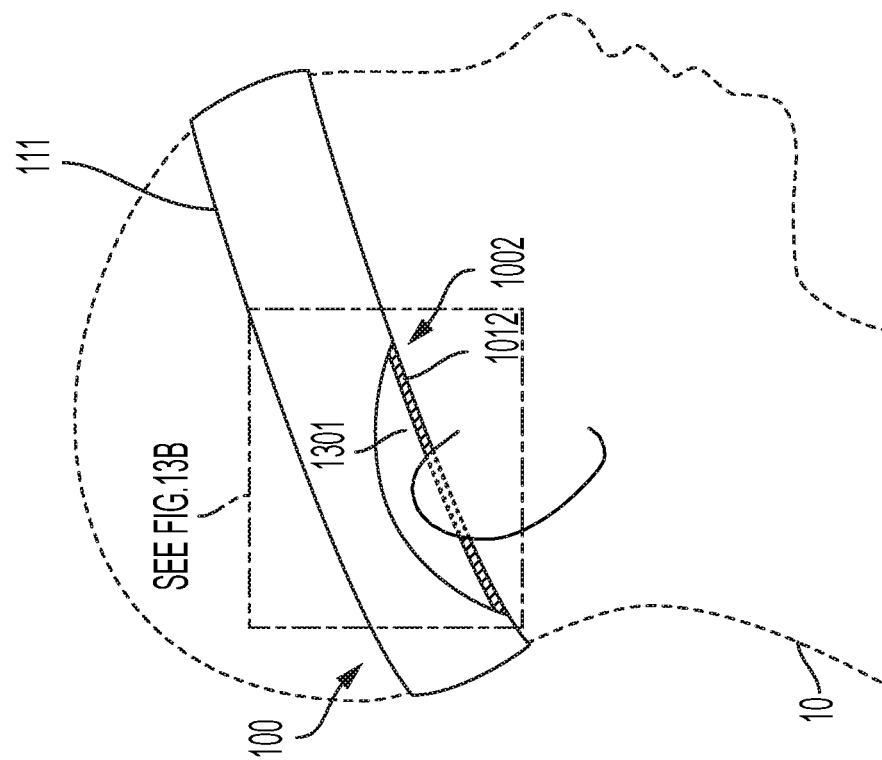
FIG. 13A illustrates a schematic side view of an embodiment of a wearable device having an above-ear electrode with an open 'bow string' design.

FIG. 13A illustrates a schematic side view of an embodiment of wearable device 100 having an above-ear electrode 1002 with an open 'bow string' design and an above-ear electrode 1004 having a closed 'bow string' design, and FIG. 13B is an expanded view thereof. FIG. 13C illustrates a schematic side view of an embodiment of wearable device 100 having an above-ear electrode 1004 with an closed 'bow string' design.

Above-ear electrode 1002 may include a strip of flexible conductive material 1012, connected at each end to body 111 of wearable device 100. Body 111 of wearable device 100 may have an area cut out above above-ear electrode 1002 which may allow conductive material 1012 to move freely. When wearable device 100 is placed on the head of user 10, downward pressure may be distributed along the length of conductive material 1012, which may increase the contact area and signal quality, and may provide a comfortable fit for user 10.

Variations of shape of the conductive material 1012 that contacts the user's ear are possible. For example, as shown in FIG. 13A, body 111 may define an aperture, illustrated as an inner region 1301 of body 111, and may be open and may be semicircular in shape, allowing conductive material 1012 to collapse toward body 111 when worn. Conductive material 1012 may be curved to form to user's 10 ear. Comfortable conductive rubber ear contacts may be provided to provide fit to keep the wearable device 100 on the head, comfort, as well as contact for conductivity from conductive material 1012. The conductive rubber 1012 may rest on top of the user's ear (for example, in the region between the top ear tip and the head). The ear of user 10 generally does not extend through inner region 1301, but body 111 would be between the ear and the head, with the ear sitting outside of inner region 1301 during regular wear.

Conductive material 1012 may be, for example, conductive rubber. In an example, conductive material 1012 may be formed from silicon rubber infused and/or coated with carbon. In some embodiments, conductive material 1014 may be formed from thermoplastic elastomer infused with carbon, and coated a PEDOT conductive polymer layer. Other suitable conductive materials may also be used.

Similarly, above-ear electrode 1004, as shown in FIG. 13C, may include flexible conductive material 1014 (for example, formed from conductive rubber) and may be shaped with a bottom portion 1024 and a top portion 1034 to define an open aperture with a perimeter generally semicircular in shape, allowing bottom portion 1024 to collapse towards top portion 1034 and body 111. Conductive material 1014 may be curved on a bottom portion 1024 to form to user's 10 ear. Comfortable conductive rubber ear contacts may be provided to provide fit to keep the headband or wearable apparatus on the head, comfort, as well as contact for conductivity from conductive material 1014.

In use, upper portion 1034 may contact the top of an ear of user 10, for example, as wearable device 100 shifts during sleep. The conductive rubber 1014 may rest on top of the user's ear (for example, in the region between the top ear tip and the head). The ear of user 10 generally does not extend through inner region 1301, but body 111 would be between the ear and the head, with the ear sitting outside of inner region 1301 during regular wear, and bottom portion 1024 and top portion 1034 in contact with the region in and around the top ear tip and the head of user 10.

Conductive material 1014 may be formed of the same or similar materials to that of conductive material 1012.

Figure 14:
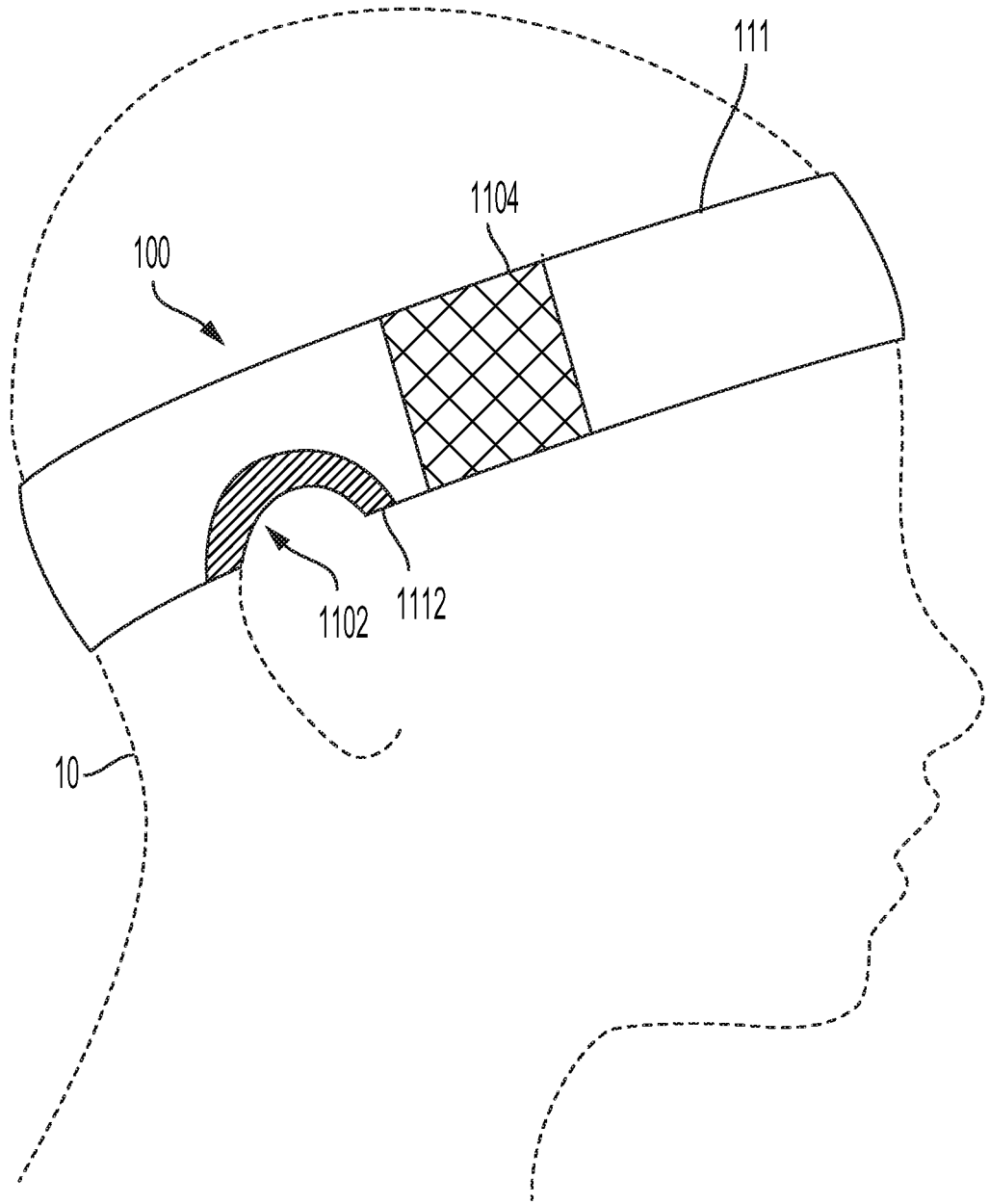
FIG. 14 illustrates a side schematic view of an embodiment of wearable device 100 having an above-ear electrode 20''' shaped to contact the upper and rear surface of an ear of a user.

FIG. 14 illustrates a side schematic view of an embodiment of wearable device 100 having an above-ear electrode 1102 shaped to contact the upper and rear surface of an ear of user 10.

Shaped above-ear electrode 1102 may comprise a strip of flexible conductive material 1112 (e.g. rubber), connected to body 111 of wearable device 100. The electrode material 1112 may be shaped to contour around the upper and rear surface of the ear which may increase the skin contact area and aid in fitting.

Conductive material 1112 may be formed of the same or similar materials to that of conductive material 1012.

A stretchable or elastic portion 1104 of body 111 of wearable device 100 may allow fitting a multitude of head sizes while maintaining proper positioning of the electrodes above and behind the ears.

Figure 15B:
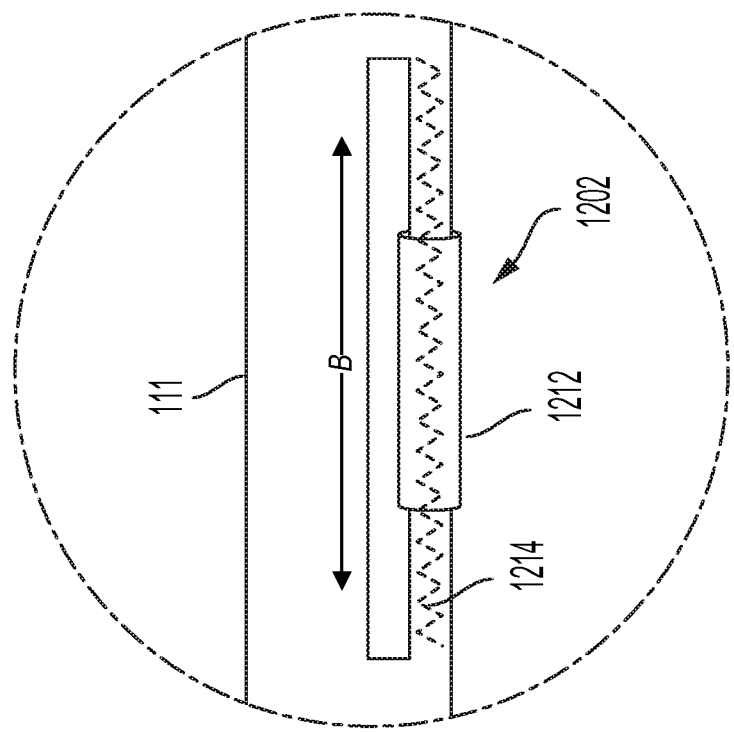
FIG. 15B is an expanded view thereof, according to an embodiment.
Figure 15A:
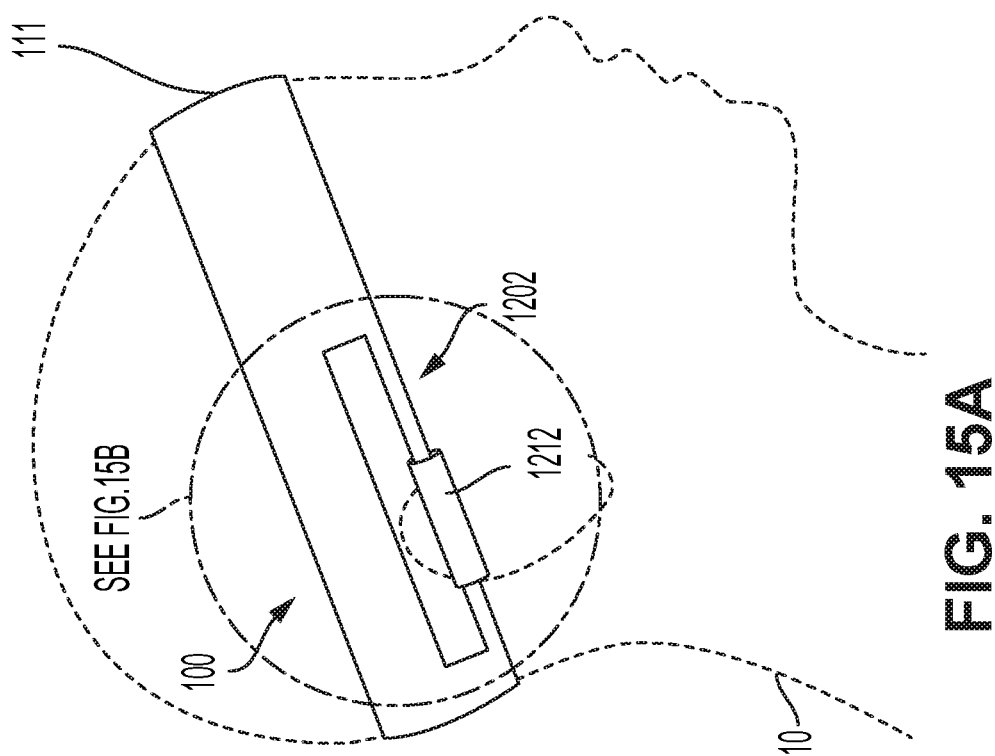
FIG. 15A illustrates a side schematic view of an embodiment of wearable device having a movable above-ear electrode.

FIG. 15A illustrates a side schematic view of an embodiment of wearable device 100 having an above-ear electrode 1202 which may be movable to provide for skin contact on a variety of head shapes, and FIG. 15B is an expanded view thereof.

FIGS. 15A and 15B illustrate movable above-ear electrode 1202, with a conductive tube 1212 contacting an exposed conductive wire or thread 1214. The conductive tube 1212 contacts the wire 1214, independent of where it is placed along the open area. The wire 1214 then conveys the sensed bio-signals to the electronics module 32.

Conductive tube 1212 may be hollow and generally cylindrical in shape, or other suitable shape to allow movement in direction illustrated by arrow B.

Conductive tube 1212 may be formed of the same or similar materials to that of conductive material 1012.

Due to signal quality requirements, it may be desirable to place electrode(s) in areas where there is little hair, such as above or behind the ear. Because the bitragion frontal arc (distance between the ears, across the forehead) varies considerably between individuals, portions of wearable device 100 may be required to stretch or extend (for example, as shown in FIG. 14, where 1104 illustrates an extendable portion in an otherwise non-stretchable device), or alternatively, movable electrodes such as movable above-ear electrode 1202, may provide for placement of the electrode in contact with an ear of user 10.

In some embodiments, bio-signal sensors 20 may be integrated in body 111 at ear contacting portion 14, to cover an ear of user 10, for example, with a generally rectangular or generally circular contact or conductive sensor formed from silver ink or other material incorporated with body 111.

It will be appreciated that in various implementations, the shape and configuration of above-ear electrode 1002, 1004, shaped above-ear electrode 1102, and movable above-ear electrode 1202 may be coordinated with the shape and configuration of body 111 to complement each other. For example, body 111 may be configured to stretch in forehead contacting portion 12 and adjacent to ear contacting portion 14 for use with shaped above-ear electrode 1102 so as to allow more variance in body 111 while the above-ear electrode remains more fitted or is less deformable. This may allow for better conformance to a head of user 10. Similarly, a longer above-ear electrode, such as above-ear electrode 1004, may be used with a less flexible body 111, as a longer above-ear electrode may accommodate different ear sizes.

Having reference to FIGS. 16 to 19A and 19B, in some embodiments, the wearable device 100 includes an inner earpiece 144 having a conductive sensor.

Figure 16:
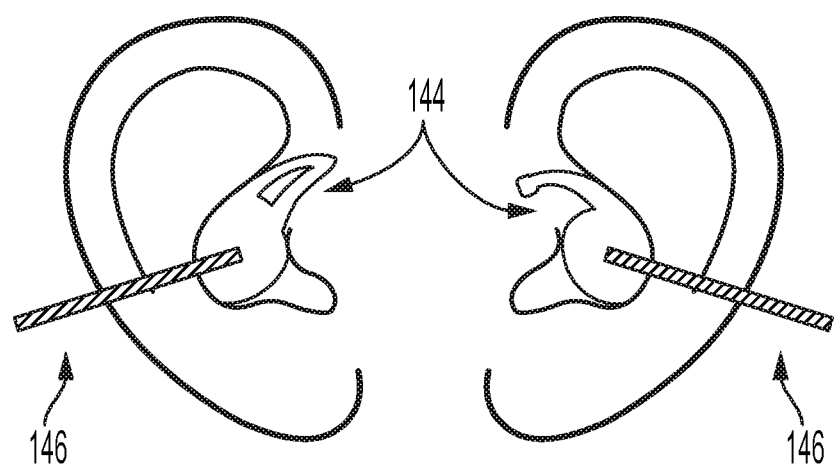
FIG. 16 is a schematic view of an inner earpiece conductive sensor, according to an embodiment.

As shown in FIG. 16, inner earpiece 144 may be shaped to form to the auricle of an ear of user 10. Inner earpiece 144 may be a conductive sensor and connect to signal transmission line 146. In some embodiments, inner earpiece 144 may have conductive material similar or the same to conductive material 1012 described herein. Inner earpiece 144 may thus form an inner-ear sensor to contact an ear canal, for example, outer ear canal, of user 10.

Signal transmission line 146 may be a wire or other similar conductive material, and connect to electronics module 32.

Figure 17:
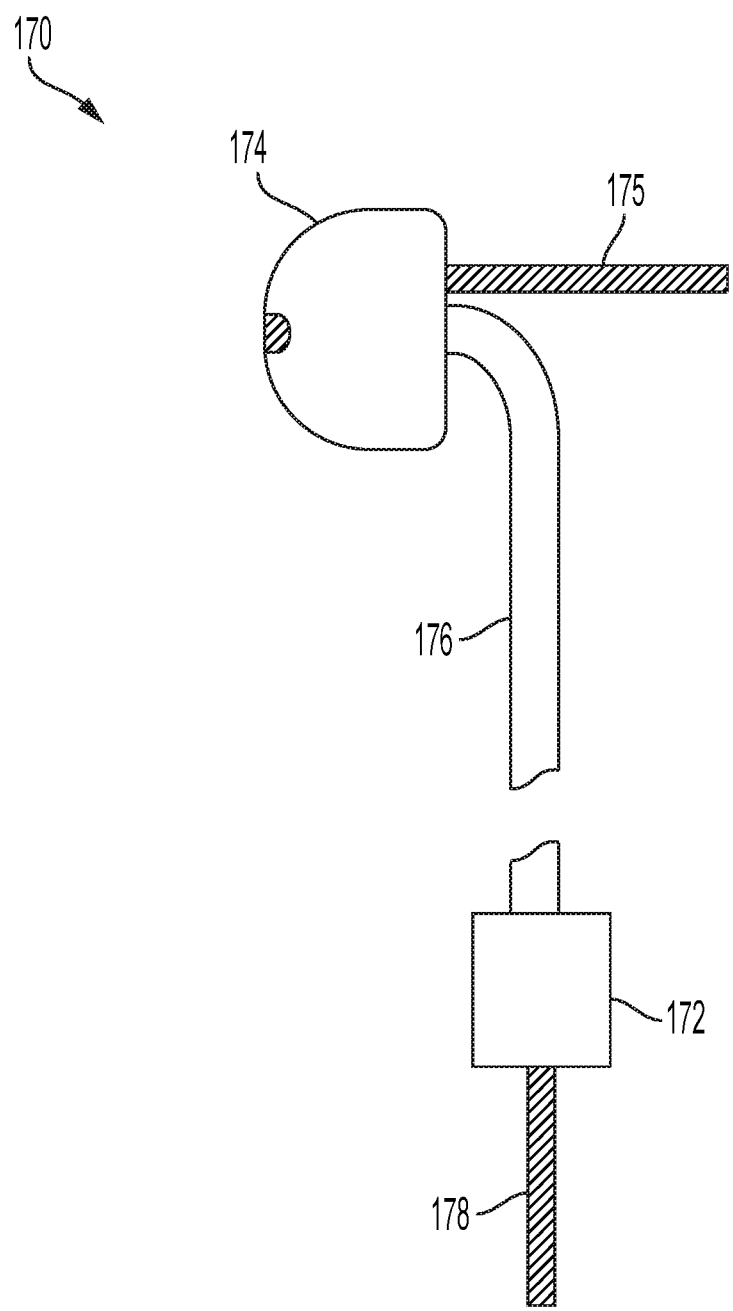
FIG. 17 is a schematic view of a sound delivery module, according to an embodiment.
Figure 18:
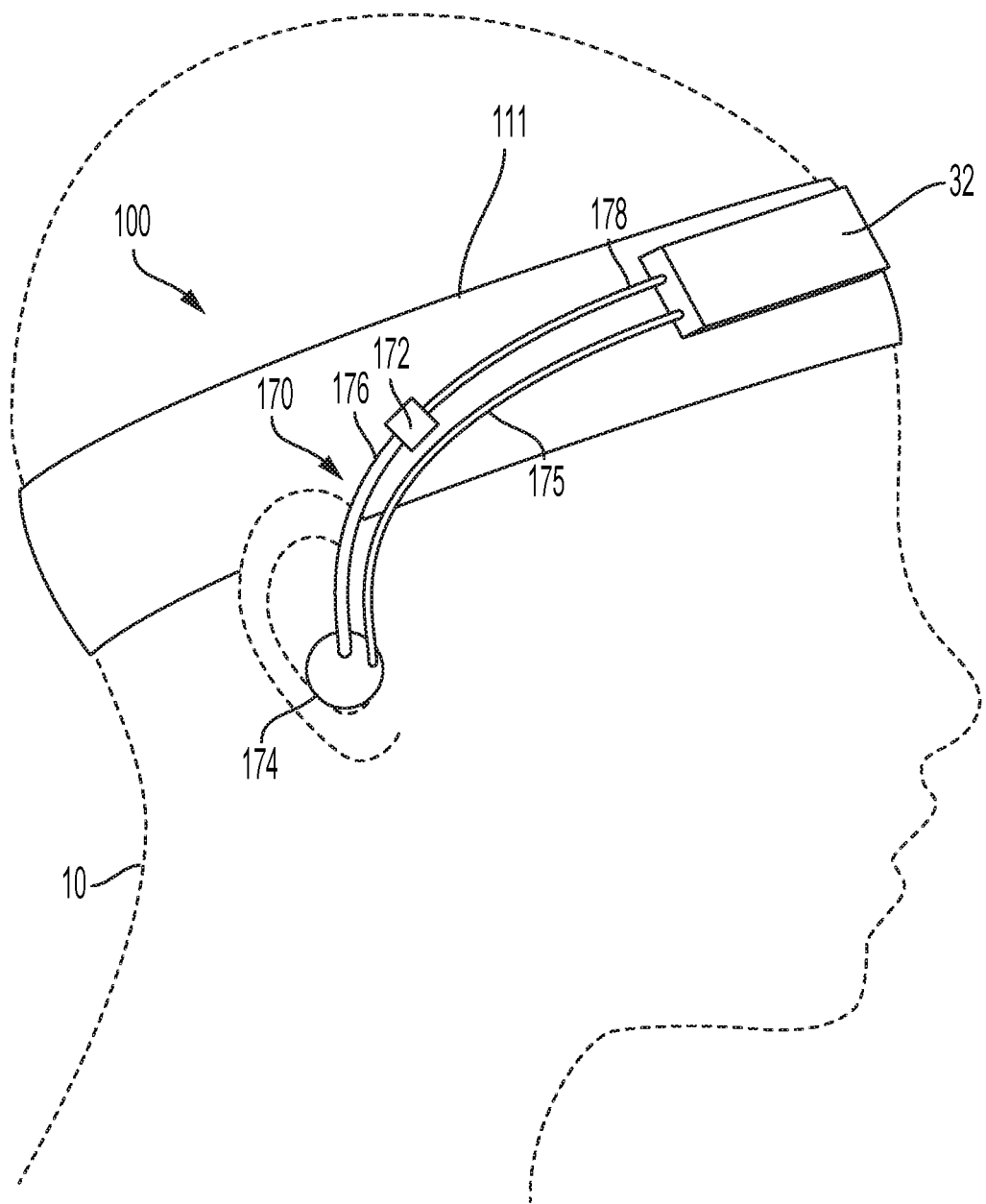
FIG. 18 is a schematic view of the sound delivery module of FIG. 17 connected to an electronics module of a wearable device, according to an embodiment.

As shown in FIGS. 17 and 18, the wearable device 100 may further include a sound delivery module 170 including a sound generator 172 connected to an inner earpiece 174 by way of a hollow tube 176. Sound generator 172 receives an audio signal from audio transmission line 178.

As shown in FIG. 17, inner earpiece 174 may be shaped to form to the auricle of an ear of user 10. In some embodiments, inner earpiece 174 may be molded, for example, heat-molded to the shape of a specific ear of user 10. Inner earpiece 174 may be a conductive sensor and connects to signal transmission line 175. In some embodiments, inner earpiece 174 may have conductive material similar or the same to conductive material 1012 described herein. In some embodiments, inner earpiece 174 may be insulative, and signal transmission line may be disposed through inner earpiece 174 to provide a conductive surface to contact an ear of user 10.

Sound generator 172 may be located at a distance, for example between 2 cm and 30 cm, from inner earpiece 174. Sound generator 172 may be a speaker or a driver to generate sound waves for travel to inner earpiece 174 by way of hollow tube 176.

In an example, hollow tube 176 is a hollow plastic tube, for example, 2-3 mm in diameter. Hollow tube 176 may be generally rigid, so as to not fold over in a manner that would interfere with the travelling sound waves.

Conveniently, distancing the sound generator from sensing (for e.g., of bio-signals of user 10 from the conductive sensor portions of inner earpiece 174) may allow for sound to be generated with less interference with sensor readings.

FIG. 18 is a schematic view of sound delivery module 170 connected to electronics module 32 of wearable device 100, in which signal transmission line 175 and audio transmission line 178 are connected to electronics module 32.

Figure 19A:
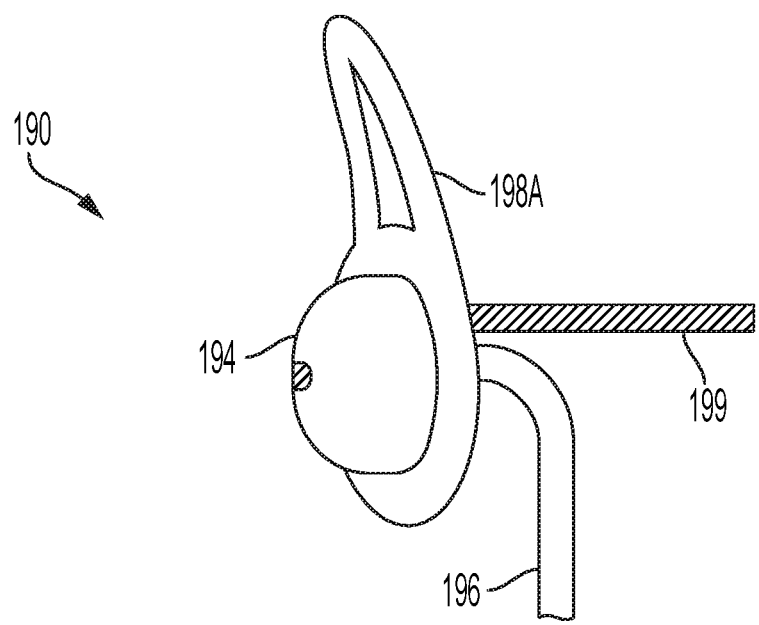
FIG. 19A is a schematic view of an inner earpiece with a conductive sensor backing frame, according to an embodiment.
Figure 19B:
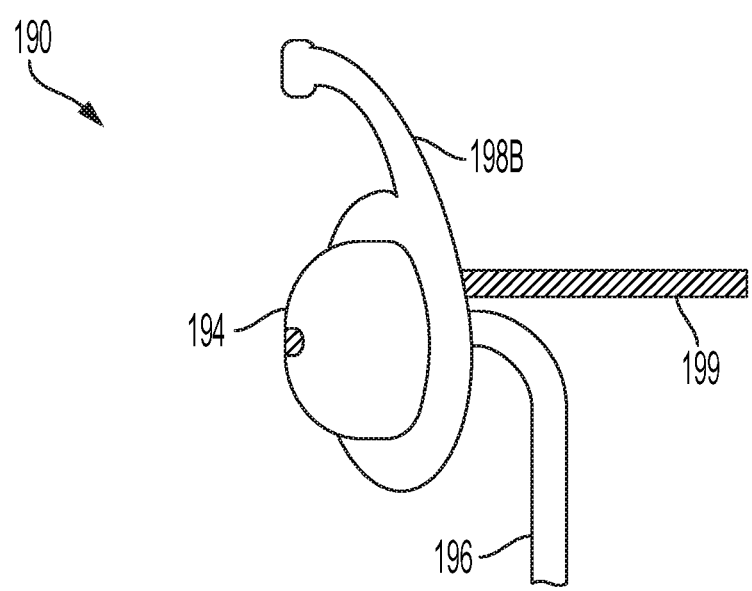
FIG. 19B is a schematic view of an inner earpiece with a conductive sensor backing frame, according to another embodiment.
Figure 23:
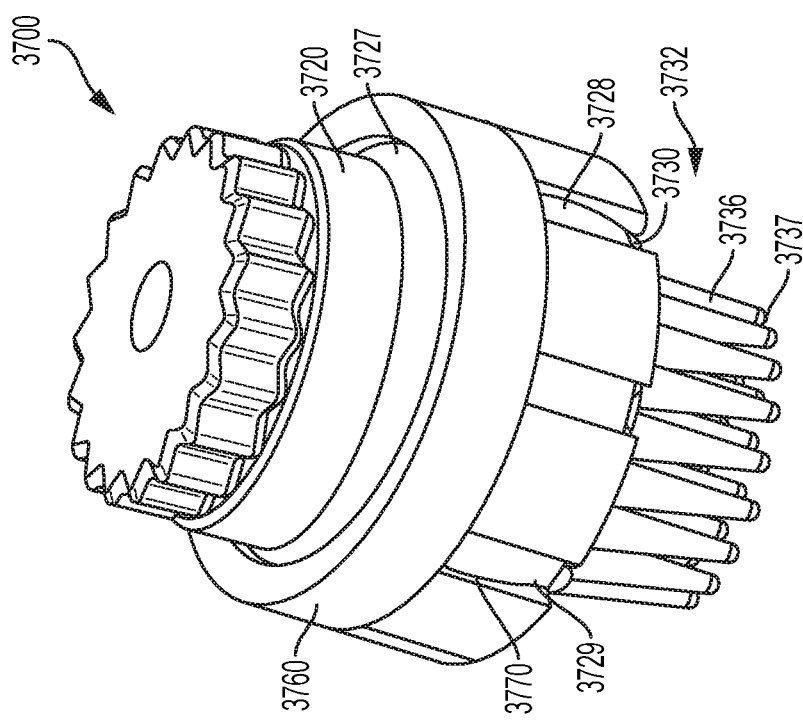
FIG. 23 illustrates a perspective view of the bio-signal sensor of FIG. 22.
Figure 22:
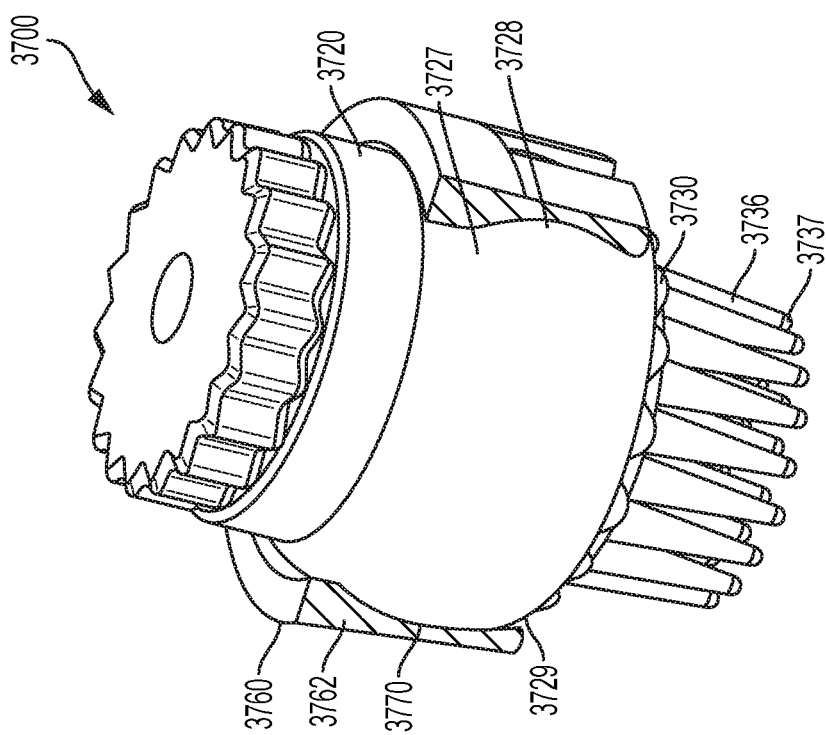
FIG. 22 illustrates a partial cross-sectional view of a bio-signal sensor, according to an embodiment.

FIGS. 19A and 19B illustrate a sound delivery module 190 including a sound generator (not shown, for example, sound generator 172) connected to an inner earpiece 194 by way of a hollow tube 196.

As shown in FIGS. 19A, 19B, inner earpiece 194 may be shaped to form to the auricle of an ear of user 10. Inner earpiece 194 may be insulative and may not be a conductive sensor.

Inner earpiece 194 may be backed by a conductive sensor such as a closed loop frame 198A, or an open loop frame 198B. Closed loop frame 198A, and similarly open loop frame 198B, may be shaped to form to the auricle of an ear of user 10.

Closed loop frame 198A connects to signal transmission line 199, which may connect to electronics module 32 to transmit bio-signals from the conductive sensor.

Conveniently use of a conductive sensor away from an inner ear canal of user 10, for example, as with closed loop frame 198A or open loop frame 198B, may avoid a build-up of ear wax, which may act as an insulator and reduce signal quality, on the conductive sensor. Such a conductive sensor may also allow for a larger surface area for the sensor to contact the user, beyond the inner ear canal.

Figure 3:
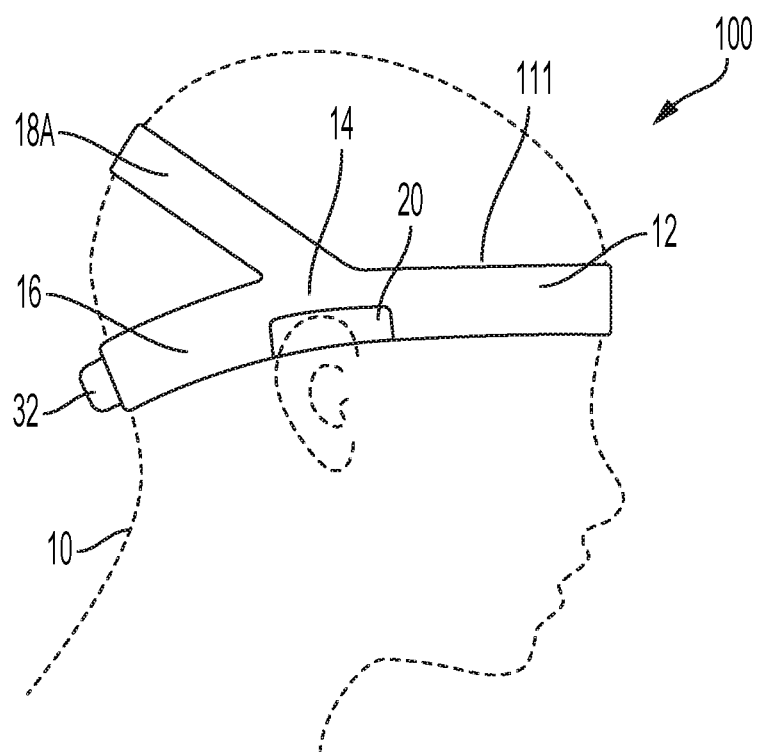
FIG. 3 illustrates a side view of an embodiment of the wearable device having a crown strap when worn by a user.
Figure 4:
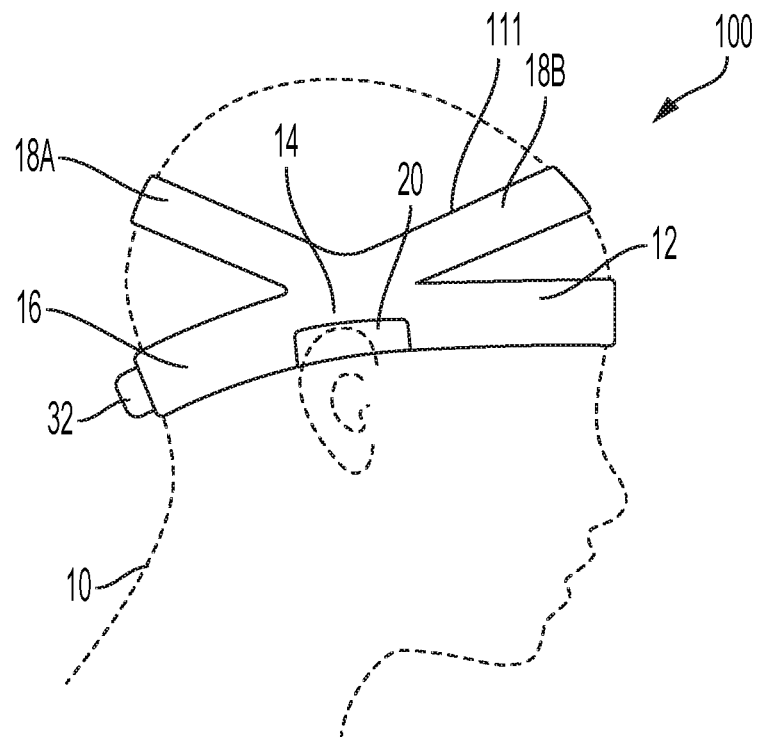
FIG. 4 illustrates a side view of an embodiment of the wearable device having a crown strap and a top strap when worn by a user.

As shown in FIGS. 3 to 5, in some embodiments, body 111 of wearable device 100 may include at least one overhead support strap. The at least one support strap may provide additional support above the head and distributes forces on the head over a greater area. In some embodiments, the overhead support straps are placed in a front-to-back orientation or a side-to-side orientation. In some embodiments, the overhead support straps are placed in a side-to-side orientation. In some embodiments, the at least one overhead support strap are joined to the loop at the ear contacting portions 14. In some embodiments, the at least one overhead support strap includes a crown strap 18A, a top strap 18B or a combination thereof. The side-to-side orientation provides forces that may be partially opposed by a strap elsewhere in the device. For example, at least some of the forces acting on the user's head from the top strap 18B may be opposed by the occipital contacting portion 16 of the loop. Similarly, at least some of the forces acting on the user's head from the crown strap 18A is opposed by the forehead contacting portion 12 of the loop. In contrast, for a front-to-back strap to have an opposing force, the device may require a chin strap or other strap exerting forces on a lower surface of the skill.

Bio-signal sensors located where there is hair may be selected for their ability to obtain a signal despite an impedance that may be created by presence of hair. With reference to FIGS. 6 and 7, in some embodiments, the apparatus includes at least one hair-penetrating bio-signal sensor 22 located on the at least one support strap, such as crown strap 18A, top strap 18B, the occipital contacting portion 16, or both. In some embodiments, hair-penetrating bio-signal sensor 22 may be disposed at other locations on body 111, including forehead contacting portion 12 and ear contacting portions 14. Hair-penetrating bio-signal sensor 22 may be a pin sensor, or a sensor with prongs (similar for example to prongs 3536 discussed in further detail below) to extend through a user's hair to contact skin 11.

Example embodiments of a hair-penetrating bio-signal sensor 22 are described below with reference to FIGS. 20 to 27. A hair-penetrating bio-signal sensor 22 may be integrated in a section of body 111 of wearable device 100 that is rigid or reinforced, for example, with reinforcing member 131. Hair penetrating bio-signal sensor 22 may also be integrated into an aperture or track defined by body 111 that allows for lateral movement of hair penetrating bio-signal sensor along body 111. Hair penetrating bio-signal sensor 22 may thus be affixed in a position, for example, by way of a corresponding threads on hair penetrating bio-signal sensor 22 rotated to capture part of body 111 and provide a friction fit.

Figure 24:
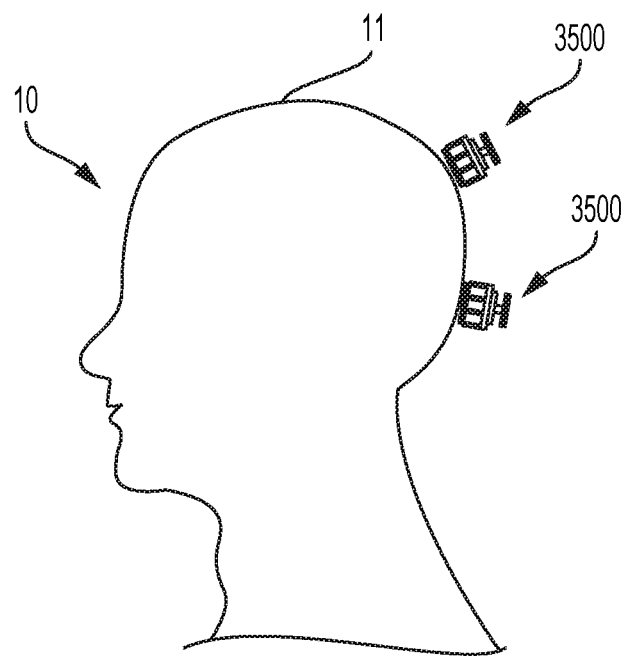
FIG. 24 illustrates a schematic view of placement of bio-signal sensors on a user, according to an embodiment.
Figure 25:
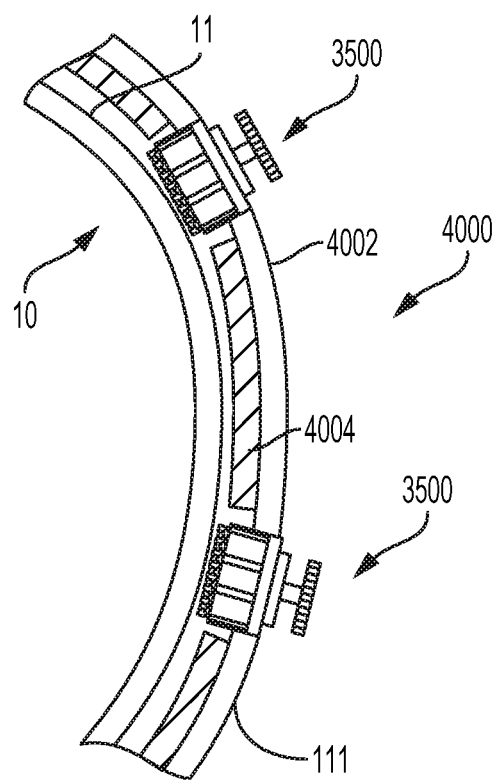
FIG. 25 illustrates a schematic view of placement of bio-signal sensors on a user, according to an embodiment.

In accordance with an aspect of the embodiments described herein, body 111 may include sensors such as bio-signal sensors 3500 for obtaining bio-signals from the scalp or skin 11 of user 10. With reference to FIG. 24, there is provided a bio-signal sensor 3500. The sensor 3500 is configured to receive a bio-signal from a user 10, preferably, from the user's head or through the skin 11 of user 10. With reference to FIG. 25, the bio-signal sensor 3500 can be included on an apparatus 4000, for example on a support portion 4002 such as body 111 of wearable device 100. The apparatus 4000 optionally includes at least one deformable portion 4004, for example, made from foam, connected to the support portion 4002 to provide comfort and/or support when the apparatus 4000 is worn by the user 10.

With reference to FIGS. 20 and 21, the bio-signal sensor 3500 includes a body 3520, having a spherical portion 3528; an electrode 3530 extendable into the body 3520, the electrode 3530 having a contact end 3532 configured to receive an electrical bio-signal from a user's 10 skin 11, wherein in response to a downward force acting on the bio-signal sensor 3500 to urge the bio-signal sensor 3500 against the user's skin 11 and upon contact with the skin 11 of user 10, the electrode 3530 is configured for movement into the body 3520 along a movement axis 3522; an actuator 3540 operatively connected to the electrode 3530 for urging the electrode 3530 out of the body 3520 along the movement axis 3522 toward an extended position, wherein in the absence of the downward force, the electrode 3530 is disposed in the extended position; and a contact adjuster 3550 connected to the electrode 3530, the contact adjuster 3550 includes a handle 3552 manipulatable by the user to reduce noise the electrical bio-signal caused by impedance of the user's hair.

In use, a force having a downward component is applied to urge the bio-signal sensor 3500 against the skin 11 of user 10 to receive an electrical signal from the user 10. The electrode 3530 moves along the movement axis 3522 into an electrode receiving space 3524 of body 3520 from an extended position toward a retracted position (see, for example, FIG. 21). However, the user's hair may impede the ability of the bio-signal sensor 3500 to receive an electrical signal from the skin 11 of user 10. For example, the user's hair may form a barrier (or "mat") that acts as an insulation layer between the contact end and the user's skin. The insulation layer impedes or prevents the receiving of the electrical signal. As such, in some embodiments, the bio-signal sensor 3500 is configured to reduce the impedance effects of the user's hair.

In some embodiments, the contact end 3532 of the electrode 3530 includes a collection plate 3534 and a plurality of prongs 3536 extending from the collection plate 3534. Each prong includes a distal tip 3537 for contacting the skin 11 of user 10. Whereas with an electrode having a single contact surface, the user's hair may form a mat under the single contact surface, an interstitial volume 3538 defined by the prongs 3536, the collection plate 3534, and the skin 11 of user 10 may receive the user's hair and reduce or prevent the formation of a mat under the distal tips 3537 of the prongs. In some embodiments, the extension of the electrode 3530 from the body 3520 in the extended position is adjustable using the contact adjuster 3550. In some embodiments, contact adjuster 3550 includes a compression fitting, or threading that mates with the electrode or the body for adjusting the extension of the electrode 3530 in the extended position. The extension of the electrode 3530 from the body 3520 accommodates users with different volumes of hair. For example, a user with thick, long hair, may have a relatively greater volume of hair, which may create an electrical barrier if a mat is formed. For such users, the extended position may be adjusted such that the electrode 3530 extends further from the body 3520 than for users with shorter or no hair.

In some embodiments, the contact adjuster 3550 is configured to move the electrode along the movement axis 3522. In some embodiments, the handle is configured for lifting the electrode 3530 when urged against the skin 11 of user 10 and repositioning the electrode for placement against the skin 11 of user 10. In some embodiments, the movement of the contact adjuster 3550 moves the plurality of the prongs 3536 collectively. For example, in some embodiments, the contact adjuster 3550 is connected to the collection plate 3534 and is configured to move the collection plate. The movement of the collection plate 3534 causes the plurality of prongs 3536, which extend from the collection plate 3534, to move.

On the application of a downward force, the electrode 3530 moves along the movement axis 3522 into the body 3520 (see FIG. 21). Where there is significant retraction of the electrode 3530 into the body 3520, the body 3520 may become proximal to the skin 11 of user 10. This may cause, for instance, the user's hair disposed under the body 3520 of the sensor 3500 may form a barrier layer preventing good contact between the electrode 3530 and the skin 11 of user 10. Thus, in some embodiments, the body 3520 includes a contact end 3526 including at least one groove 3529 for receiving at least a portion of the user's hair therein.

In order to provide better comfort for a user, the pressure of the electrode 3530 against the skin 11 of user 10 may not be excessive. In some embodiments, the distal tips 3537 of the plurality of prongs 3536 are rounded. In contrast to a pointed tip, a rounded tip distributes the force applied to the skin over a greater area. In some embodiments, the radius of the distal tip is between about 0.25 mm and about 1 mm. In some embodiments, the radius of the distal tip is about 0.5 mm. The number and spacing of the prongs 3536 are selected such that the pressure applied to the skin 11 of user 10 is not excessive and has sufficient contact area to receive good adequate signal from the user's skin while maintaining sufficient void volume between prongs 3536 to receive the user's hair. In some embodiments, the electrode 3530 has a prong density of about 15 to 40 prongs per square centimeter. In some embodiments, the electrode 3530 has a prong density of about 25 pins per square centimeter.

A greater area of the contact end of the electrode 3530 may provide better electrical readings. However, when the area is too large, it may not conform well to the skin. One reason for this is that the skin is, typically, not perfectly flat. Increased area of the contact end of the electrode also increases the likelihood that the skin's curvature bends away, resulting in a loss of contact for the electrode. Thus, in some embodiments, the area of the contact end of the electrode 3530 comprising the prongs 3536, including the interstitial area between prongs, is between about 1 cm$^2$ and about 3 cm$^2$. In some embodiments, the area of the contact end of the electrode 3530 comprising the prongs, including the interstitial space between prongs, is about 1.5 cm$^2$. In some embodiments, the shape of the contact end 3532 of the electrode is round or polyhedral. The shape of the contact end 3532 may help move the user's hair to reduce or prevent the impedance effects of the user's hair.

In some embodiments, the contact adjuster 3550 is configured to rotate the electrode along a plane that is substantially perpendicular to the movement axis. The rotational movement may move the hair disposed under the sensor 3500. In some embodiments where the sensor includes a plurality of prongs 3536, the rotational movement may move the hair into the interstitial volume 3538. In some embodiments, the rotational movement of the contact adjuster 3550 is unrestricted. In some embodiments, the rotational movement of the contact adjuster 3550 is limited.

In some embodiments, the actuator 3540 includes a spring, a piston, a compressible material, or combination thereof. In some embodiments, the actuator 3540 includes a spring 3542. In some embodiments, the spring 3542 is a coil spring. The spring 3542 is disposed within the electrode receiving space 3524 such that one end is biased against an upper end 3526 of the body against the electrode 3530 such that the electrode 3530 is urged away from the electrode receiving space 3524 toward the extended position. In some embodiments, the spring 3542 biases against an upper end of the collection plate 3532 of the electrode 3530. When a downward force is applied to the sensor 3500 and when the electrode 3530 is against the skin 11 of user 10, the spring 3542 resists the movement of the electrode 3530 into the body 3520 such that a force is translated to the electrode 3530 urging it against the skin 11 of user 10.

In some embodiments, the spring 3542 is fixed on one end to the body 3520 and biased against the electrode 3530 on the other end, and wherein the contact adjuster 3550 includes a shaft 3554 extending through a compressive axis 3544 of the spring 3542 for translating rotational forces perpendicular to the movement direction from the handle 3552 to the electrode 3530, translational forces along the movement direction from the handle to the electrode, for both. In some embodiments, the compressive axis is co-axial or substantially co-axial with the movement axis 3522. In some embodiments where the spring 3542 is a coil spring, the coils of the coil spring are coiled around the shaft 3554 of the contact adjuster 3550.

In some embodiments, the actuator 3540 includes a plurality of actuators (not shown) corresponding to the plurality of prongs 3536. In some embodiments, the plurality of actuators individually bias the prongs against the skin 11 of user 10. This may allow, for instance, better conformity of the sensor against the skin 11 of user 10 as the skin may not be perfectly flat.

The electrical bio-signal received by the electrode 3530 may be transmitted to a signal receiver, such as a processor or other computing device (not shown). In some embodiments, the signal receiver receives the electrical bio-signal from the body 3520 of the sensor. In some embodiments, the body includes a conductive portion 3527 for receiving the electrical bio-signal from the electrode. The conductive portion 3527 may be a conductive coating, a conductive material integrated into the body, or both. In some embodiments, the conductive coating is a conductive paint, such as a metallic paint, or a carbon paint. In some embodiments, the metallic paint includes silver, gold, silver-silver chloride, or a combination thereof. In some embodiments, the conductive material is a carbon-loaded plastic, or a conductive metal. In some embodiments, the body is 3D printed with a conductive material incorporated therein. In some embodiments, impedance between the electrode and a connection on the sensor for a wire from the signal receiver is less than about 1 kΩ. In some embodiments, the impedance between the electrode and the connection on the sensor is from about 1Ω to about 500Ω. In some embodiments, the connection is on the body 3520 or on a housing 3760 of a sensor 3700 shown in FIG. 19

In some embodiments, the actuator 3540 electrically connects the electrode 3530 to the body 3520. For example, an electrical bio-signal may be transmitted from the electrode 3530 to the body 3520 via the actuator 3540. In some embodiments where the actuator 3540 includes a spring 3542, the spring 3542 is conductive. For example, a spring 3542 biased on one end against a collection plate 3534 and on the other end against the body 3520, the spring may act as a conductor.

In accordance with an aspect of the embodiments described herein, body 111 may include sensors such as bio-signal sensors 3700 for obtaining bio-signals from the scalp or skin 11 of user 10. Having reference to FIGS. 22 and 23, in some embodiments, a sensor 3700 includes a gimbal 3770 configured to orient the electrode 3730 normal or substantially normal to the skin 11 of user 10. A normally oriented electrode 3730 may have better contact with the user's skin. For example, where prongs 3736 are the same length, a normal orientation prevents the angular contact with the user's skin where certain prongs are not lifted off from the user's skin. Further, where the electrode 3730 contacts the skin at an angle, one or more of the prongs 3736 may be pushed up by the hair. In some embodiments, body 3720 includes a spherical portion 3728, wherein the sensor further includes a housing 3760 defining a joint portion 3762 configured to receive the spherical portion 3728 of the body 3720 such that the gimbal 3770 includes the spherical portion 3728 and the joint portion 3762. In some embodiments, the spherical portion 3728 is removably receivable by the joint portion 3762. In some embodiments, the interface between the joint portion 3762 and the spherical portion 3728 includes a friction reducing agent. In some embodiments, the friction reducing agent is a carbonaceous material. In some embodiments, the carbonaceous material is integral to at least a portion the body 3720, the housing 3760, or both. In some embodiments, the housing 3760 includes an electrical connection portion for establishing an electrical connection between the sensor 3700 and a signal receiver.

In some embodiments, body 3720 includes at least one groove 3729 for receiving at least a portion of the user's hair therein.

In some embodiments, at least a portion of the conductive portion 3727 is disposed in or on the spherical portion 3728. In some embodiments, the electrical bio-signal received from the electrode 3720 is transmitted to the housing 3760 from the body 3720. In these embodiments, the signal received may connect to the housing 3760. In some embodiments where a friction reducing agent is included, the friction reducing agent includes or is a conductivity modifier to improve impedance. In some embodiments, the conductivity modifier is a metal powder, graphite, carbon nanotubes, metal-coated glass or plastic beads. For example, where the friction reducing agent is a carbonaceous material integral to the body 3720, the carbonaceous material may provide both friction reduction and conductivity. In some embodiments, a wire on a support portion 4002 of a head-mounted apparatus 4000 is connected at one end to the sensor 3700.

Figure 27:
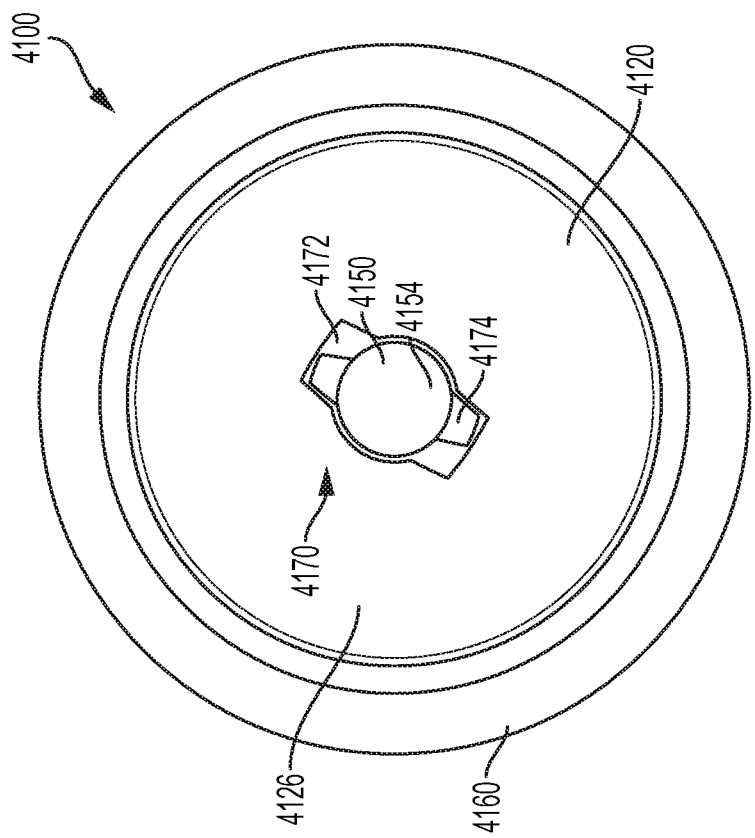
FIG. 27 illustrates a top view of the bio-signal sensor of FIG. 26.
Figure 26:
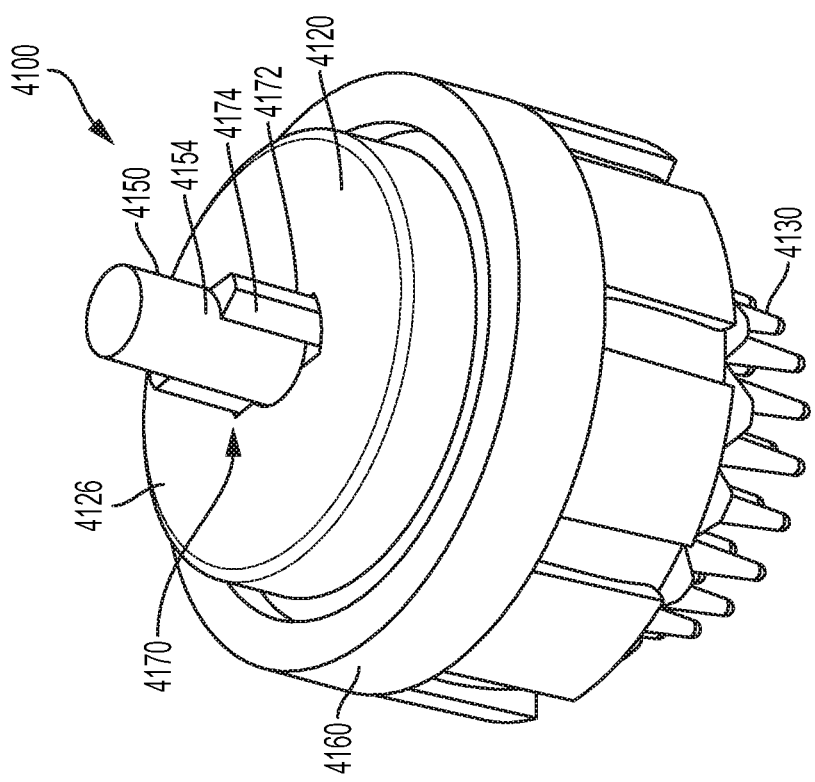
FIG. 26 illustrates a perspective view of a bio-signal sensor, according to an embodiment.

Having reference now, to FIGS. 26 and 27, in some of the embodiments where the rotational movement is limited, the sensor 4100 includes a rotational limiter 4170 for limiting the rotational movement of the electrode 4130. If the hair is rotated excessively in a single direction, the hair may become wrapped or tangled. In some embodiments, the rotational limiter allows an oscillatory movement along a rotational axis for the electrode to get between the user's hairs. In some embodiments, the rotational limiter limits the rotational movement to at least about 0.25 radians. In some embodiments, the rotational limiter 4170 includes a slot 4172 and a key 4174 configured to rotate restrictively within the slot 4172. The movement of the electrode 4130 with respect to the body 4120 are limited by the slot 4172 and the key 4174. In some embodiments, the upper end 4126 of the body 4120 defines the slot 4172 and the shaft 4154 of the contact adjuster 4150 includes the key 4174. In some embodiments, the rotational limiter includes a stop disposed in the body, the electrode, the shaft, or any combination thereof. In some embodiments, a housing 4160 is configured to receive body 4120.

In some embodiments, a light connected to the processor indicates a brain state at the sensor 3500 or sensor 3700. In some embodiments, the brightness or color of the light is modified according to an event in the brain, such as an event related potential, a continuous EEG, a cognitive potential, a steady state evoked potential, or combination thereof. In some embodiments, the light is integral with the sensor or mounted proximate the sensor on a support portion of a head-mounted apparatus.

In some embodiments, body 111 may include other bio-signal sensors 20 such as non-contact electrodes 180.

Figure 28:
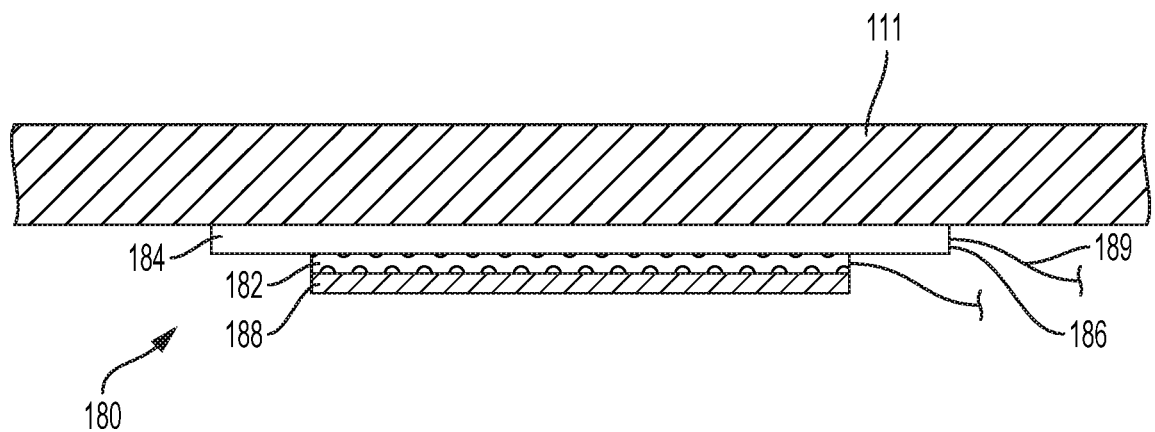
FIG. 28 illustrates a non-contact electrode, according to an embodiment.

Having reference to FIG. 28, in some embodiments, non-contact electrodes 180 include a conductive layer 182 and a conductive noise layer 184 with a dielectric layer 186 disposed therebetween. The conductive noise layer 184 reduces the noise in the signal obtained by the electrode 180. The conductive noise layer 184 may be an active guard or a ground plane. In some embodiments, a dielectric layer 188 is applied to a user facing side of the conductive layer 182. The conductive layer 182 connects to electronics module 32 or sensor electronics via a wire 189.

Figure 29:
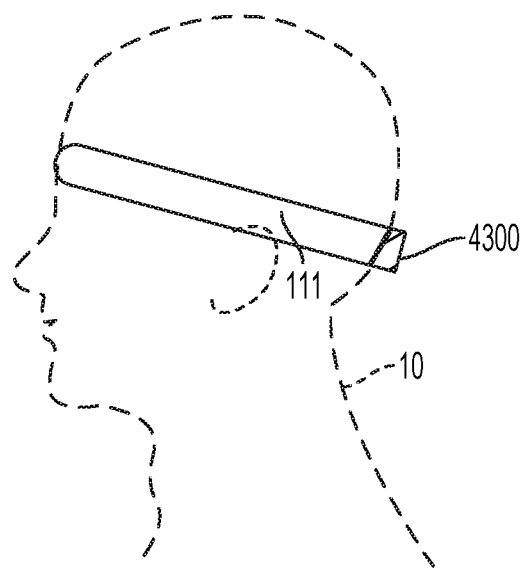
FIG. 29 illustrates a side view of a user wearing a wearable device having a capacitive electrode, according to an embodiment.
Figure 30:
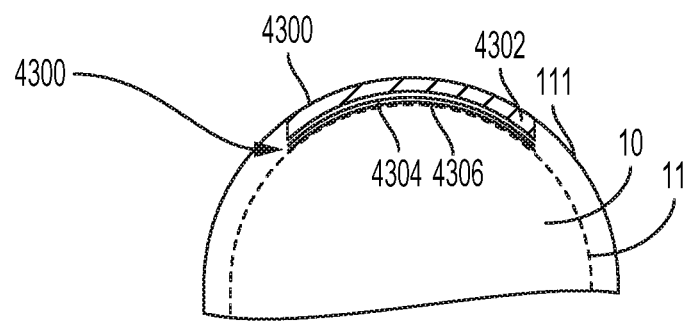
FIG. 30 illustrates a partial top view of the wearable device of FIG. 29.

In some embodiments, a non-contact electrode may take the form of capacitive electrode 4300, as shown in FIG. 29, or other suitable capacitive electrode. FIG. 29 illustrates a side view of user 10 wearing a wearable device 100 having a bio-signal sensor in the form of a capacitive electrode 4300, according to an embodiment. FIG. 30 illustrates a partial top view of wearable device 100 of FIG. 29.

In some embodiments, body 111 includes one or more capacitive electrodes 4300, for example, positioned adjacent a top of the head of user 10 and the back of the head of user 10, as shown in FIG. 29. Electrodes 4300 may be disposed in body 111 of wearable device 100 to receive bio-signal data of user 10. In some embodiments, received bio-signal data may include brainwave data of user 10. In some embodiments, capacitive electrode 4300 may be a noncontact electrode that does not come into direct contact with skin 11 of user 10.

Body 111 may include a compressible foam 4302 which may conform to the shape of the head of user 10. In some embodiments, compressible foam 4302 may be formed of an open cell foam, such as open cell foam material known to a user skilled in the art. Compressible foam 4302 may be compressible such that when the wearable device 100 is affixed to the head of user 10, compressible foam 4302 conforms to the head of user 10. In use, the compressible foam 4302 may be compressed and conform to the head of user 10 by clinching of body 111 to secure wearable device 100 to user 10.

In some embodiments, on a surface of compressible foam 4302 adjacent user's 10 head, a conductive layer 4304 of capacitive electrode 4300 is secured to compressible foam 4302.

Conductive layer 4304 may have a thickness between 1 and 100 µm, in an example 20 µm. Conductive layer 4304 may be formed of a conductive material such as a polymer substrate with conductive ink, a conductive polymer, conductive fabric or a flexible PCB.

Conductive layer 4304 may be insulated adjacent the head of user 10 with an insulating layer 4306. Insulating layer 4306 forms a dielectric medium, creating a capacitive coupling between conductive layer 4304 and skin 11 of user 10. In some embodiments, hair or other body tissue of user 10 may further contribute to the dielectric formed by insulating layer 4306 and the capacitive coupling may form across hair or other body tissue of user 10. Hair of user 10 may be compressed and held in place by the pressure exerted by compressible 4302.

Insulating layer 4306 may have a thickness between 1 and 100 µm, in an example 50 µm. Insulating layer 4306 may be formed of a polymer, for example, polyester.

Insulating layer 4306, by providing a minimal insulating layer between conductive layer 4304 and skin 11 of user 10, may moderate variability in the capacitive coupling between conductive layer 4304 and skin 11 of user 10 caused by variances in the properties of user's 10 hair. Insulating layer 4306 may also minimize salt bridging effects that may arise, for example, due to user 10 sweat creating a salt bridge forming an electrical connection between electrodes leading to improper readings being obtained by the electrodes.

In some embodiments, conductive layer 4304 may be connected to the HMD 110 or sensor electronics, for example, a signal conditioning and amplification circuit, via a wire (not shown).

In some embodiments, wearable device 100 includes an electronics module 32 including a computing device or a processor 30 for receiving the bio-signals from the at least one bio-signal sensors 20 and/or hair-penetrating bio-signal sensors 22 located on the loop. Electronics module 32 may connect to any bio-signal sensors 20, 22 or other sensors described herein. Electronics module 32 may also contain a power source such as one or more batteries, for powering electronics module 32. In some embodiments, the electronics module 32 is located on the forehead portion 12, the ear contacting portion 14, the occipital portion 16, or the support straps 18 such as crown strap 18A, and top strap 18B. Electronics module 32 may be mounted on a portion of body 111 that is reinforced and inflexible, so as to structurally support electronics module 32. Electronics module 32 may be selectively mountable and selectively removable on body 111 of wearable device 100. In some embodiments, electronics module 32 may be integral with body 111, and not releasable.

In an embodiment, the electronics module 32 is located on the occipital contacting portion such that when worn, the electronics module 32 is located at an indent in the skull under the occipital bone. Placement of the electronics module 32 at the occipital portion reduces protrusion may provide better aerodynamics and weight distribution if the device is worn while performing activities requiring movement, and provide a sleeker appearance as compared to placement at the forehead contacting portion 12 or the support strap 18. When the device is designed for a user who is lying down, such as when sleeping, the electronics module 32 may be placed at a point on the device that minimizes the formation of stress points, such as that created by the user's head against a pillow, and minimizes the possibility that the device will snag or catch on a pillow, blanket, etc., for example, if the user moves in their sleep. In some embodiments, electronics module 32 may be located at or adjacent forehead contacting portion 12, which may reduce interference of electronics module 32 with a user's sleep, regardless of whether the user sleeps on their back or side, with any sort of pillow.

In some embodiments, the electronics module 32 additionally includes electronics components such as at least one of an analog front end to amplify and filter the bio-signal data, an analog-to-digital converter, a memory to store the bio-signal data received from the bio-signal sensors 20, a wireless radio for communication with a remote processor, a battery, a charging circuit, and a connector for charging the battery. In some embodiments, the electronics package is fixedly or removably mounted on the device. In some embodiments where the electronics package is removably mounted on the device, the loop includes a pouch for containing the electronics module 32.

In some embodiments, one or more electronics components, for example, a pre-amp, may be disposed outside of electronics module 32, and integrated into body 111 of wearable device 100.

Figure 31A:
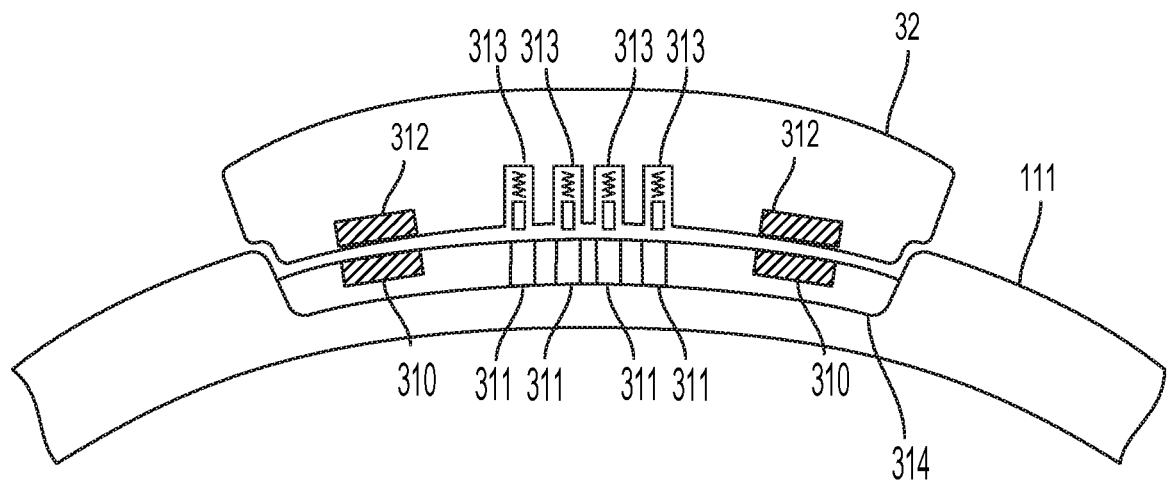
FIG. 31A is a top schematic cross-sectional view of an electronics module connected to wearable device, according to an embodiment.
Figure 31B:
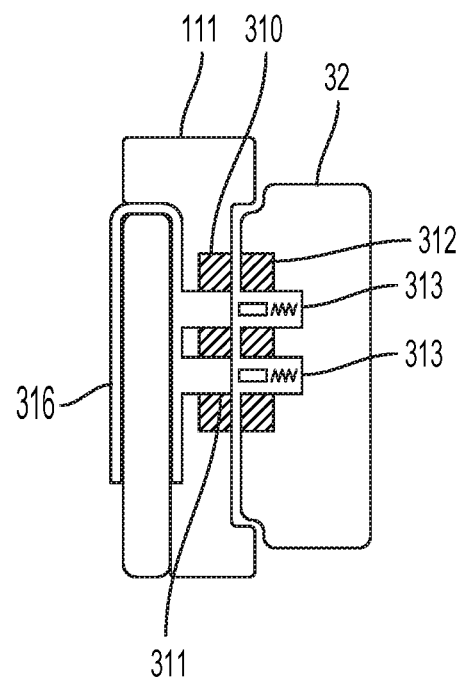
FIG. 31B is a side schematic cross-sectional view of the electronics module connected to the wearable device of FIG. 31A.

FIG. 31A is a top schematic view of electronics module 32 connected to, in an example, forehead contacting portion 12 of body 111 of wearable device 100. FIG. 31B is a side schematic view of electronics module 32 connected to forehead contacting portion 12 of body 111 of wearable device 100.

As shown in FIGS. 31A, 31B, electronics module 32 may include magnets 312 to cooperate with corresponding magnets 310 in body 111, to retain electronics module 32 against body 111. Electronics module 32 may be thus selectively removable from wearable device 100.

Electronics module 32 may further include spring pins 313 to provide an electrical contact with contacts 320 in body 111. Contacts 311 may further be connected to bio-signal sensors 20, 22 in wearable device 100.

As shown in FIG. 31A, magnets 310 and contacts 311 may be embedded in a substrate 314, made, for example of rubber. Substrate 314 may be generally rigid so as to structurally support electronics module 32.

In some embodiments, contacts 311 may connect to a flexible printed circuit board 316, for example, as shown in FIG. 31B.

Figure 32:
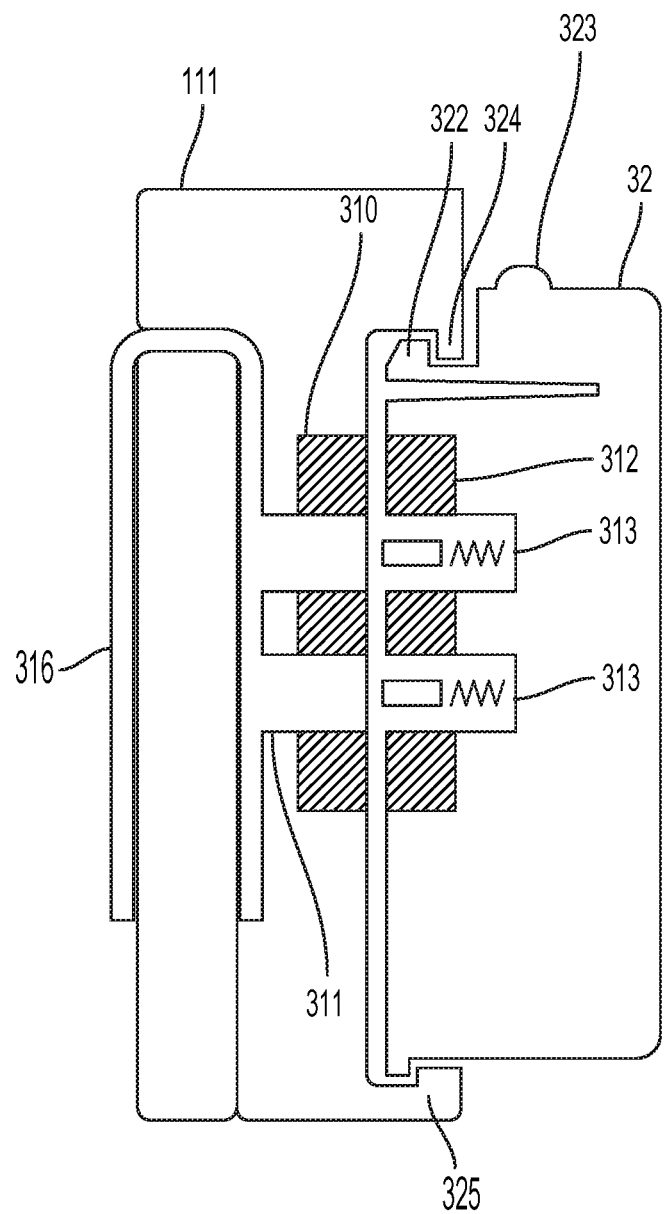
FIG. 32 is a side schematic cross-sectional view of an electronics module connected to a wearable device, according to another embodiment.

FIG. 32 is a side schematic view of electronics module 32 connected to forehead contacting portion 12 of body 111 of wearable device 100. Electronics module 32 may be configured as shown in FIGS. 31A and 31B and described above, with the addition of a clip 322, to engage with receiving hook 324 to further retain electronics module to wearable device 100. Body 111 may also include a retaining lip 325 to engage with a corresponding lip on electronics module 32 to further secure electronics module 32 to body 111. Protrusion 323 may be pressed to release clip 322 from hook 324 and remove electronics module from body 111.

Figure 33:
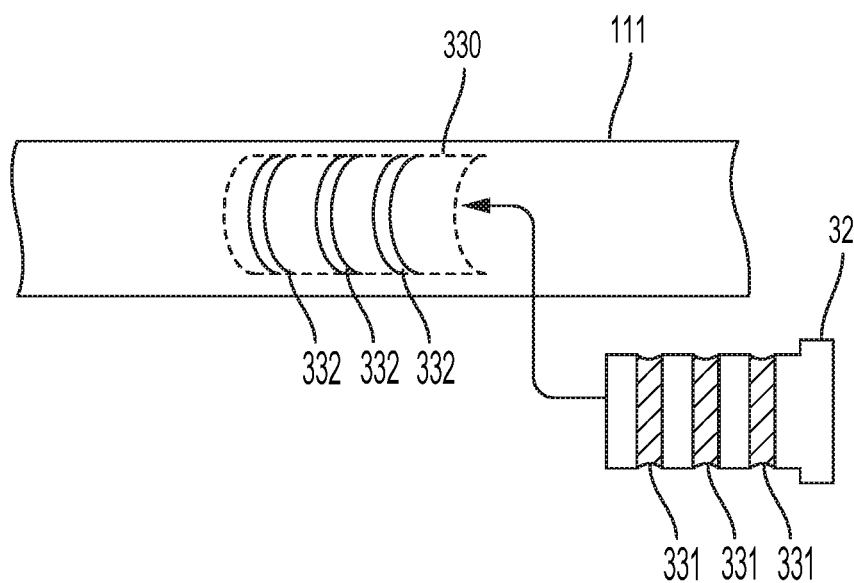
FIG. 33 is a schematic view of a pocket in a body of a wearable device for retaining an electronics module, according to an embodiment.

FIG. 33 is a schematic view of a pocket 330 in body 111 for retaining electronics module 32, in a section of body 111 that is elastic, for example, made of elastic fabric. Electrical contacts 331 on electronics module 32 may contact conductive ribs 332 of body 111. Conductive ribs 332 may be integral with body 111, for example, as conductive thread or may be other suitable conductive sensors, and may connect with bio-signal sensors 20, 22.

Figure 34A:
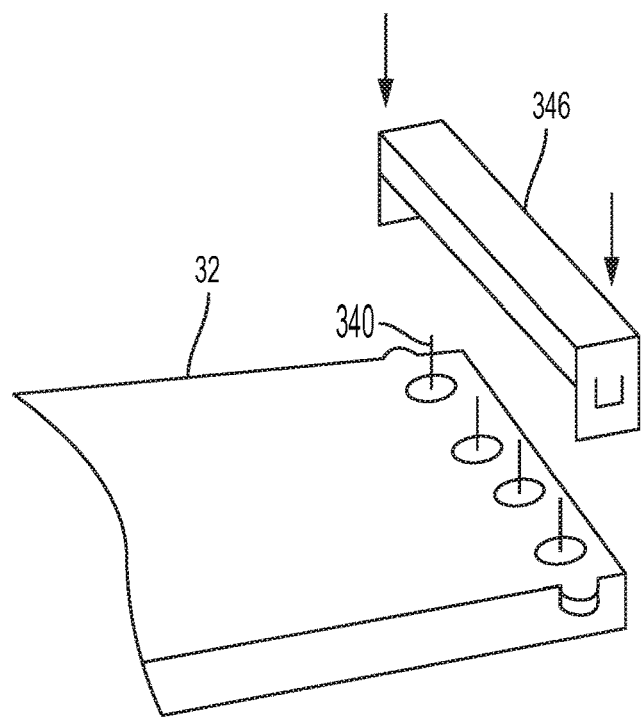
FIGS. 34A-34C illustrate schematic views of an electronics module with extruding conductive pins for contact with conductive threads, according to an embodiment.
Figure 34B:
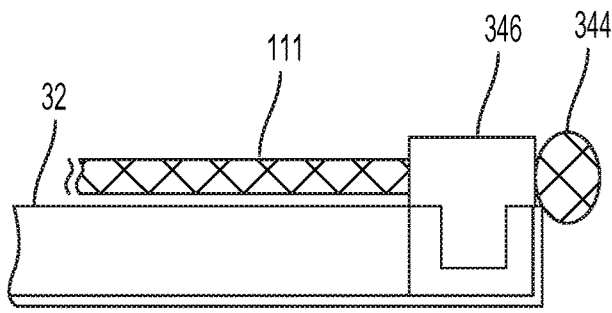
Figure 34C:
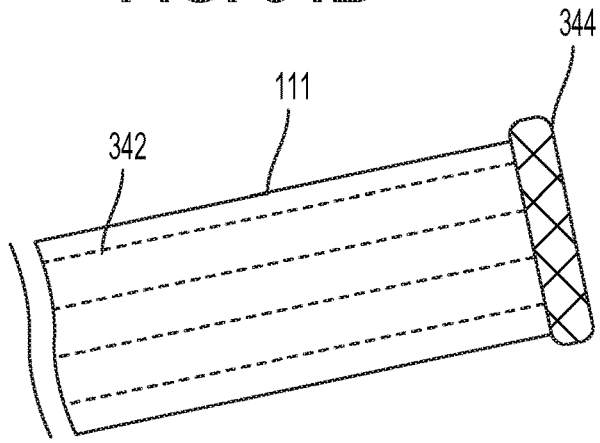

As shown in FIGS. 34A to 34C, in some embodiments electronics module 32 may have conductive pins 340 extruding from a surface, for contact with conductive threads 342, for example, on a section of body 111, and having a molded stop 344. A clip 346 may retain conductive threads 342 against conductive pins 340.

Figure 35A:
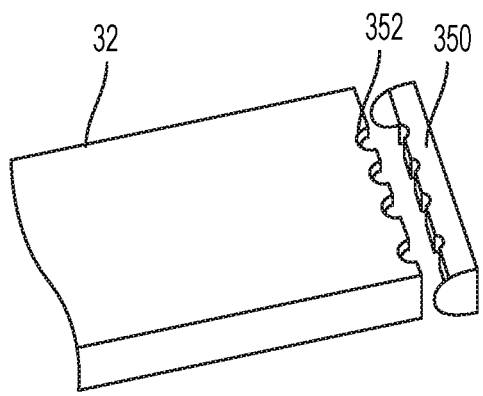
FIG. 35A, 35B illustrate schematic views of an electronics module with recesses for receiving molded contacts, according to an embodiment.
Figure 35B:
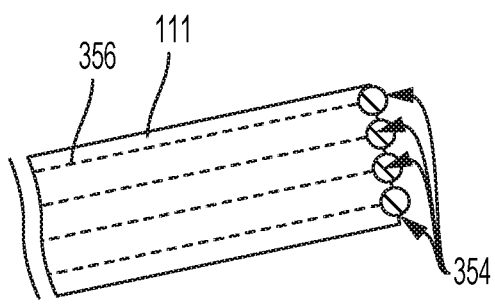

In another embodiment, as shown in FIGS. 35A and 35B, electronics module 32 may include recesses 352 to receive molded contacts 354 connected to conductive threads 356 in body 111. Clip 350 may retain molded contacts 354 in recesses 352 of electronics module 32.

Figure 36:
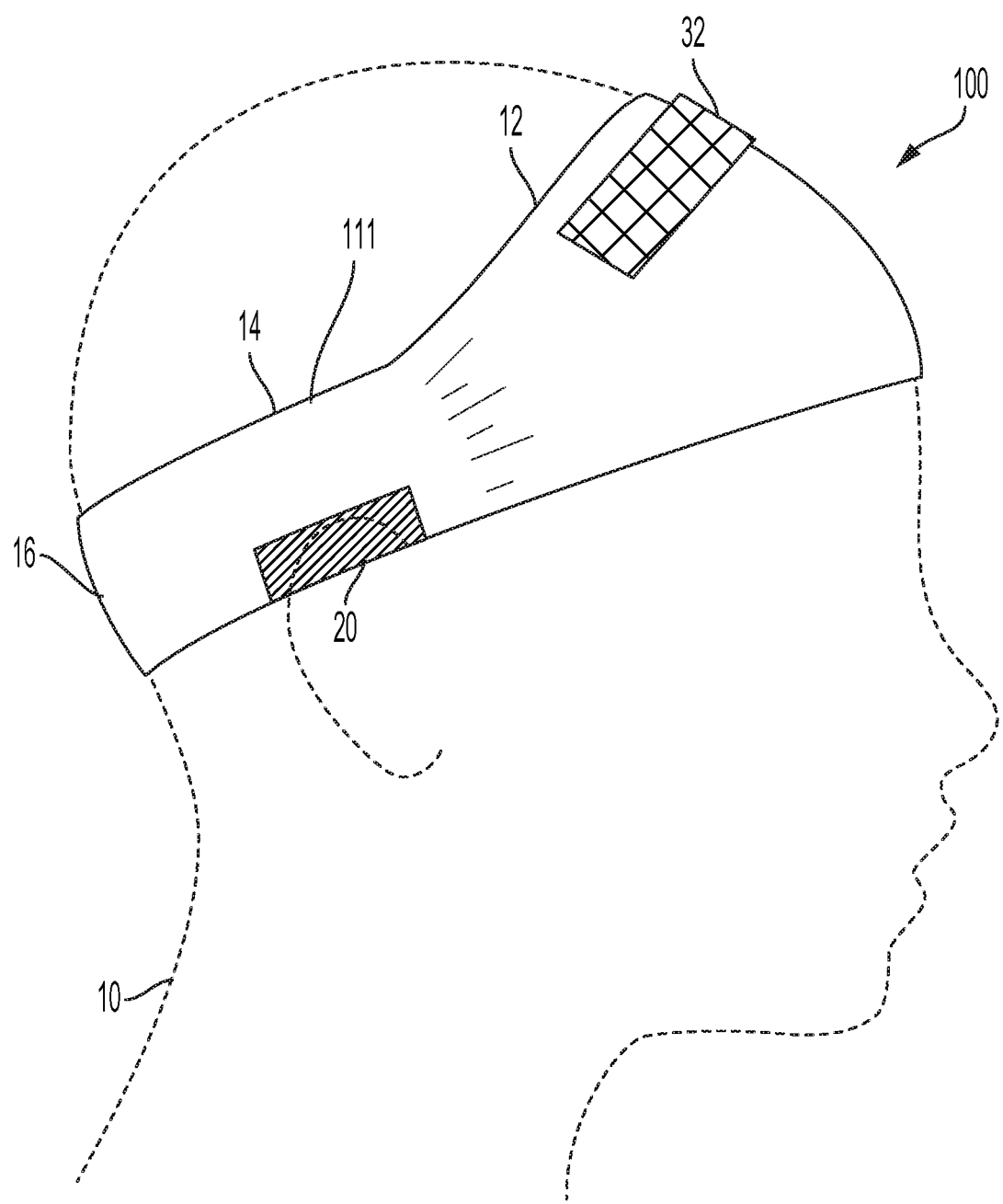
FIGS. 36 and 37 illustrate a side view of an embodiment of a wearable device having an extendable, stretchable forehead contacting portion, according to an embodiment.
Figure 37:
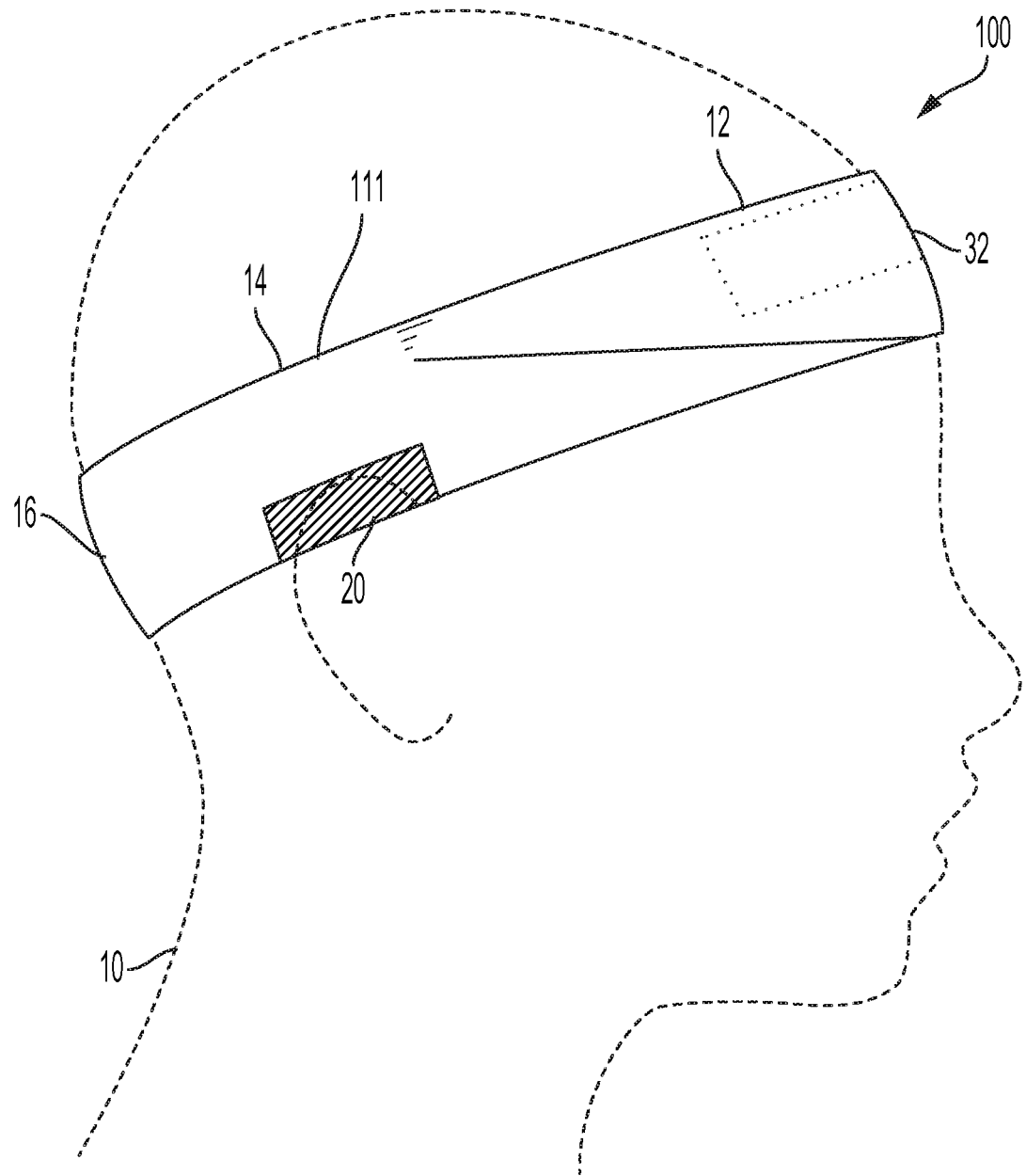

FIGS. 36 and 37 illustrate a side schematic view of an embodiment of the wearable device 100 having an extendable, stretchable forehead contacting portion 12 of body 111 where the electronics module 32 is mountable.

In this embodiment, wearable device 100 may be worn as shown in FIG. 36, with the module high on the head to allow for other wearable technology, such as a heads-up display or VR headset to be worn on the forehead. Alternatively, portion 12, along with electronics module 32, may be folded down as shown in FIG. 37 to hide the electronics module 32.

Figure 38:
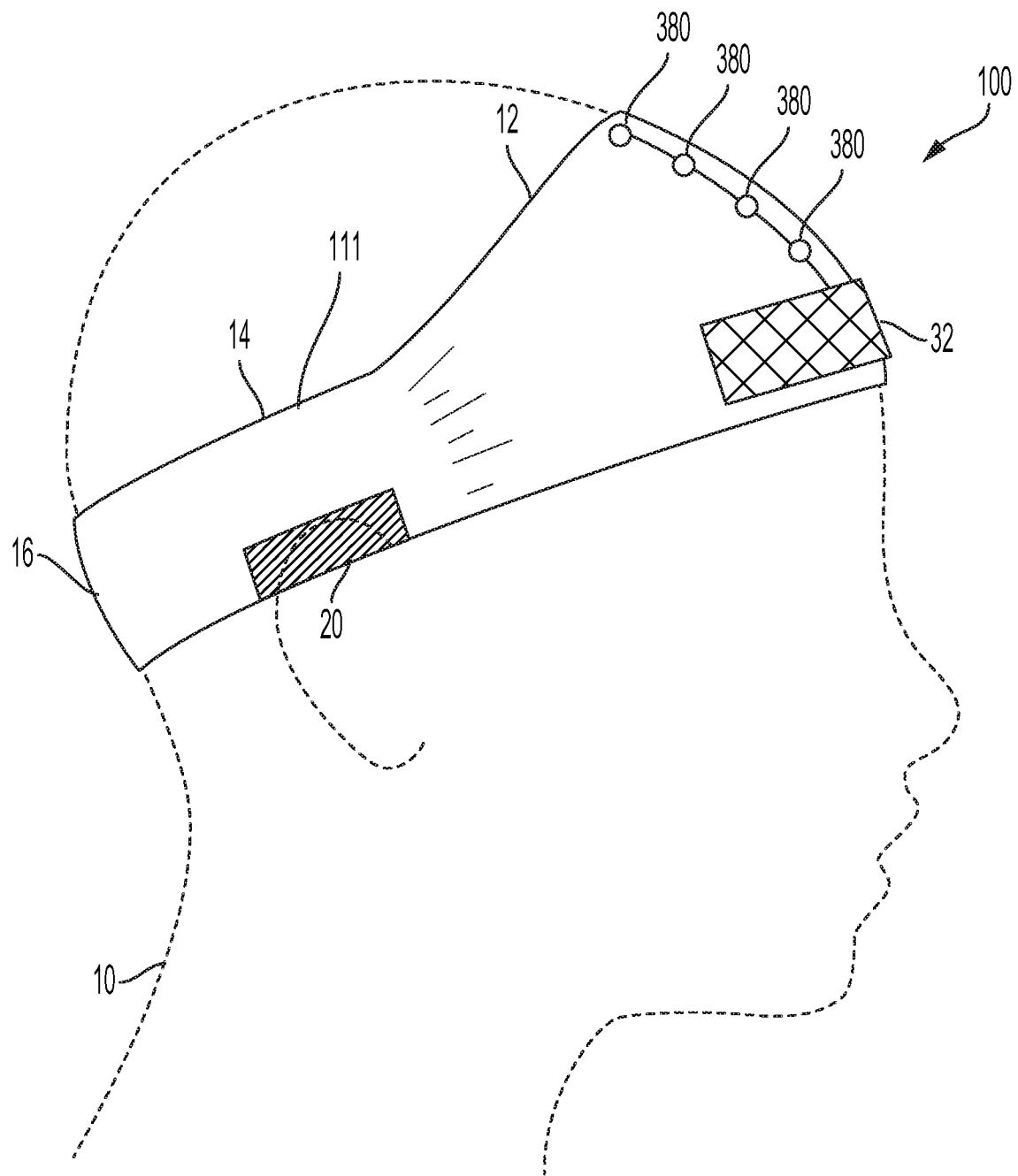
FIG. 38 illustrates a side view of an embodiment of a wearable device having an extendable, stretchable forehead contacting portion with attachment locations for auxiliary sensors, according to an embodiment.

FIG. 38 illustrates a side view of an embodiment of wearable device 100 having an having an extendable, stretchable portion 12 which has placement or attachment locations 380 for auxiliary electrodes to attach to body 111 for contact with user 10. Attachment locations 380 may provide an opening in which auxiliary electrodes or sensors may be disposed, and provide a contact surface that is conductive and pre-wired to the electronics module 32, for a connection between auxiliary electrodes or sensors and electronics module 32.

Auxiliary electrodes may be any type of through-hair sensor, and could be attached to the wearable device via snaps, clamps, etc. The extendable, stretchable portion can be pulled back over the hair, offering a large array of potential auxiliary electrode locations (for auxiliary or additional sensors, as described in further detail below).

In some embodiments, the device includes additional auxiliary sensors. In some embodiments, the auxiliary sensor is selected from an optical heart rate sensor, a pulse oximeter sensor, a gyroscope, an accelerometer, a magnetometer, or any combination thereof. In some embodiments, the device includes an optical heart rate sensor and/or a pulse oximetry sensor. In some embodiments, the optical heart rate sensor and/or the pulse oximetry sensor are located on the forehead contacting portion such that they contact the forehead or the temple region of the user's head. In some embodiments, signal data from the gyroscope, accelerometer, magnetometer, or combination thereof may be used to determine an attitude and heading reference system (AHRS) to determine the orientation of the head. Such data could be used, for example, to provide additional information when analyzing brain patterns of sleep, activity, etc. For example, analysis of a user's sleep may analyze tossing and turning in conjunction with brainwave signals.

In some embodiments, body 111 may include openings or mounting points for mounting auxiliary sensors and/or auxiliary electrodes, for example, for research purposes. In an example, openings may be defined adjacent or along the mid-line of the head of user 10.

In some embodiments, the device includes an audio emitter. In some embodiments, the audio emitter is selected from a speaker, a bone conduction transducer, a piezoelectric transducer, or combination thereof.

In various implementations, the wearable device 100 may include a tracker or other sensors, input devices, and output devices. In some embodiments, for example, the tracker is an inertial sensor for measuring movement of the device 100. It detects the 3-dimensional coordinates of the wearable device 100 and accordingly its user's location, orientation or movement. The tracker, for example, comprises one or more accelerometers and/or gyroscopes. The wearable device 100 may comprise a touch sensor for receiving touch input from the user and tactile device for providing vibrational and force feedback to the user.

In various implementations, the wearable device 100 may include feedback components (such as user effectors) to vibrate or provide some audio or visual feedback to user 10. For example, a speaker such as a waveguide speaker may be integrated into body 111 of wearable device 100. A vibrotactile feedback source may also be integrated into body 111. In some embodiments, a bone conductor transducer may be implemented into body 111.

Figure 39A:
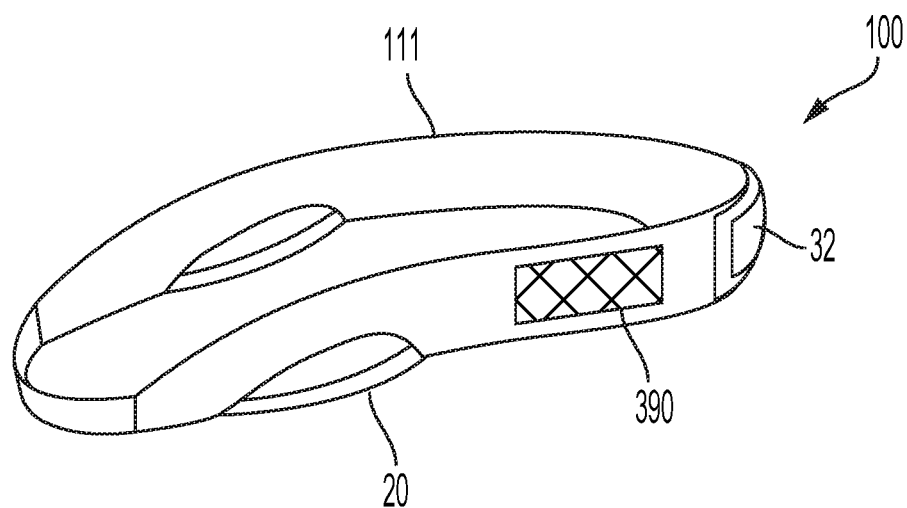
FIG. 39A is a schematic perspective view of a wearable device with a touchpad location, according to an embodiment.
Figure 39B:
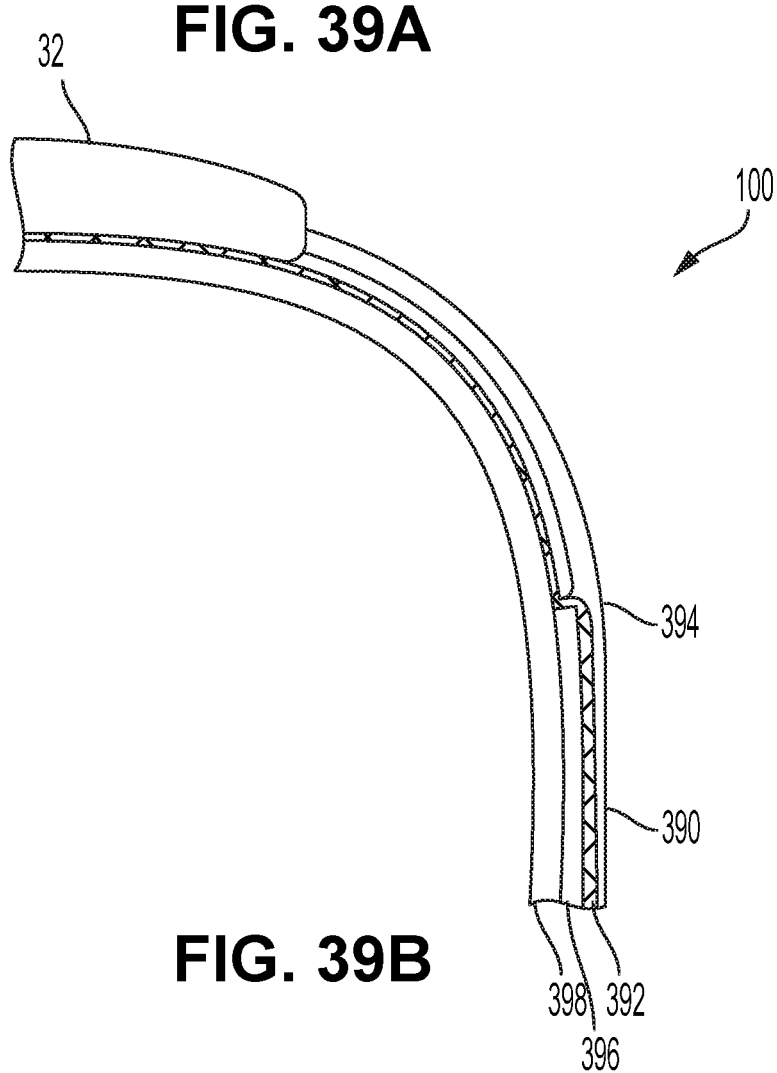
FIG. 39B is a schematic top view of the wearable device with the touchpad location of FIG. 39A.

As shown in FIGS. 39A and 39B, in some embodiments, wearable device 100 may include a touchpad location 390. Touchpad location 390 may include a touchpad sensor 392 disposed between a fabric layer 394 and two foam layers 396, 398 and connected to electronics module 32. Touchpad sensor 392 may be used to control various settings of wearable device 100, for example, by way of electronics module 32, such as volume of a sound generating component.

Figure 40:
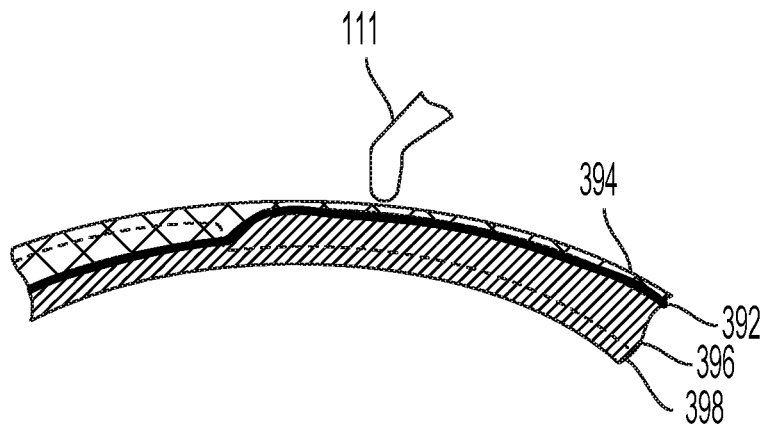
FIG. 40 illustrates a cross-sectional side view of the wearable device with the touchpad location of FIGS. 39A and 39B.

FIG. 40 illustrates a cross-sectional side view of wearable device 100 with touchpad location 390 of FIGS. 39A and 39B, for use, for example, by a finger 400 of user 10. As shown, touchpad sensor 392 may flex between foam layers.

Figure 41:
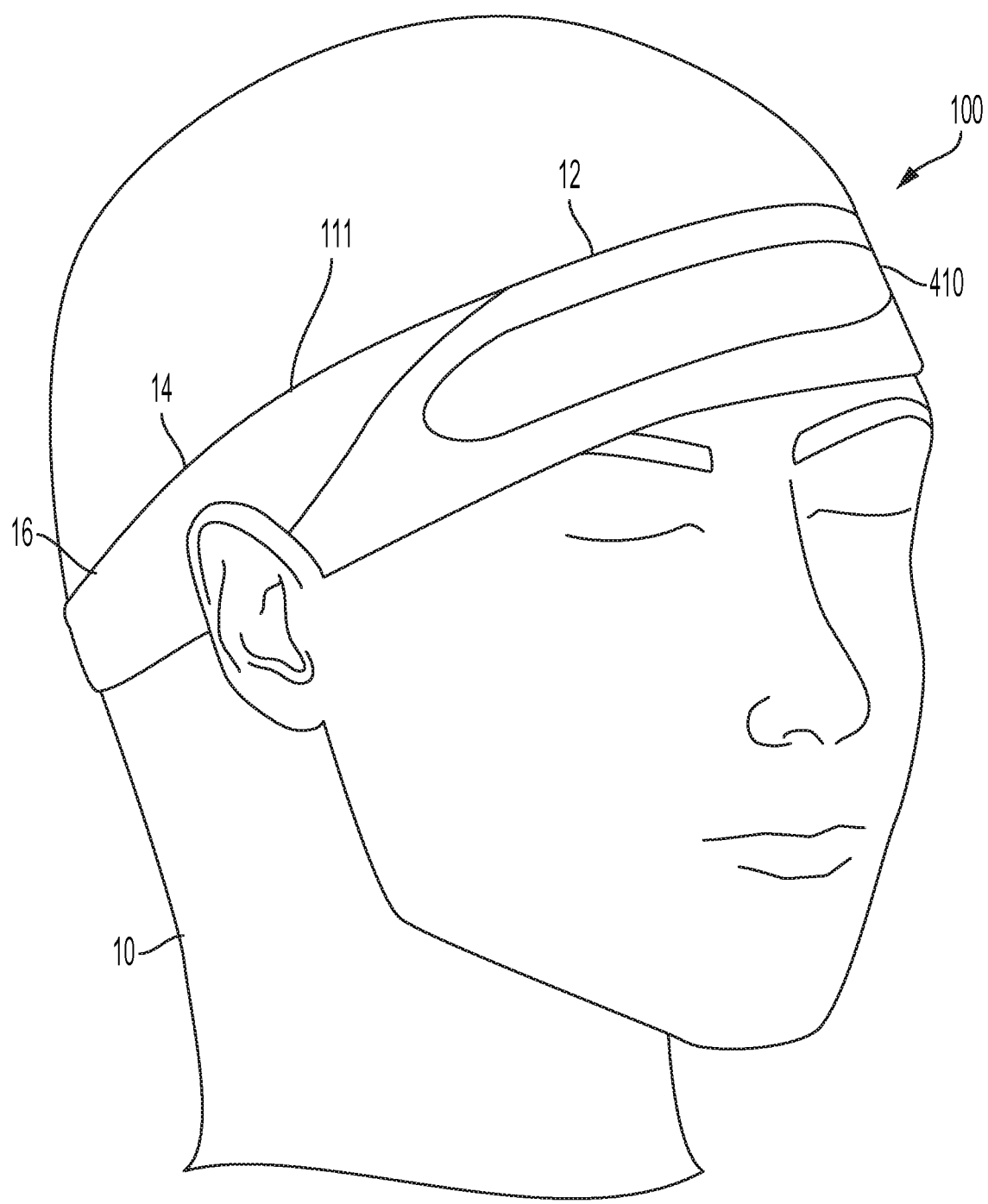
FIG. 41 is a schematic perspective view of a wearable device with an extendable, stretchable forehead contacting portion in which an OLED flexible array may be disposed, according to an embodiment.
Figure 42:
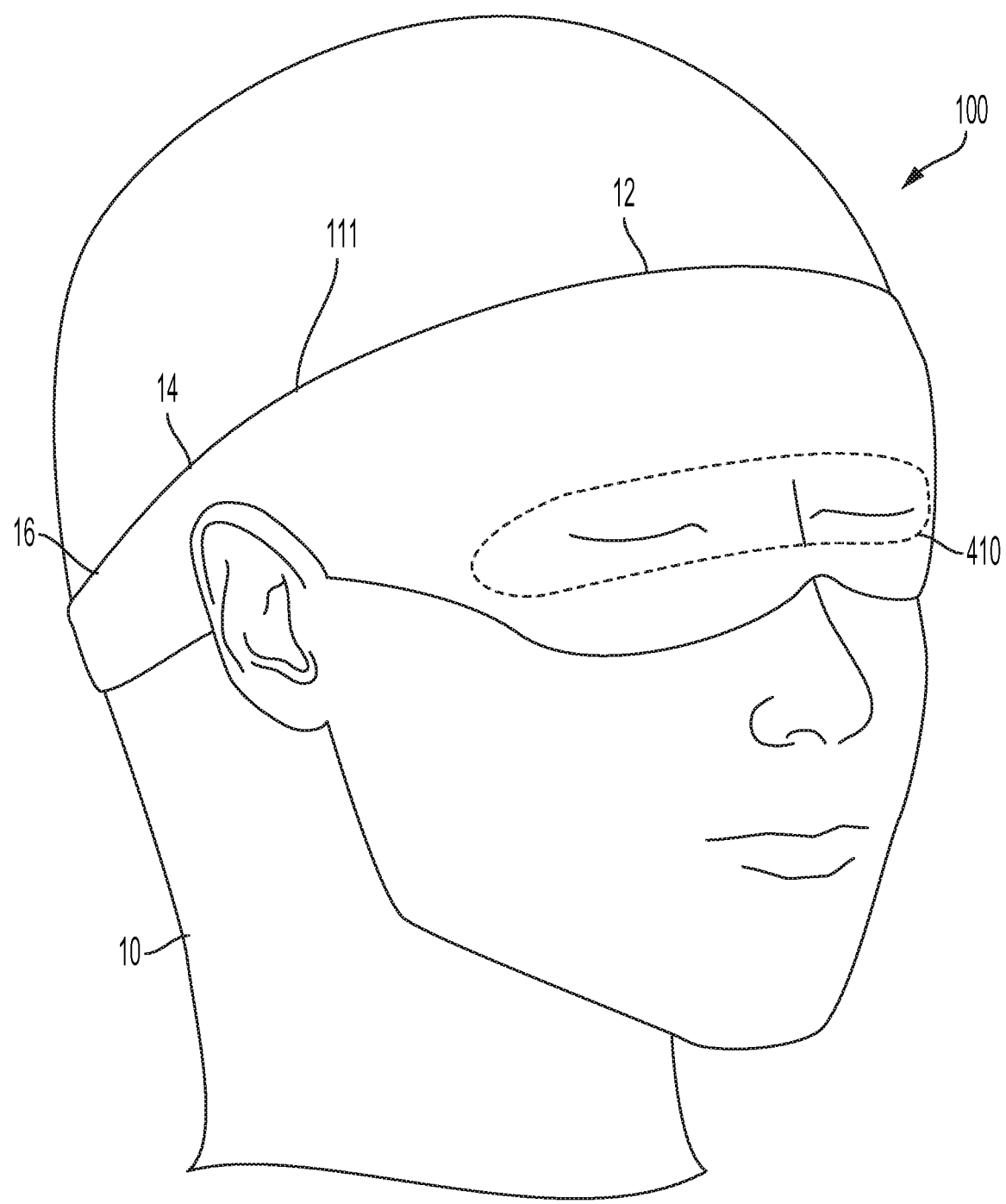
FIG. 42 is a schematic perspective view of the wearable device and the OLED flexible array of FIG. 41, in a folded down configuration.

FIG. 41 is a schematic perspective view of wearable device 100 with an extendable, stretchable forehead contacting portion 12 of body 111 in which an OLED flexible array 410 may be disposed. As shown in FIG. 42, portion 12, along with OLED flexible array 410, may be folded down for viewing by user 10. OLED flexible array 410 may be integrated into fabric of body 111, and may provide luminescence to user 10, for example, a light to prompt a user to wake.

Figure 43A:
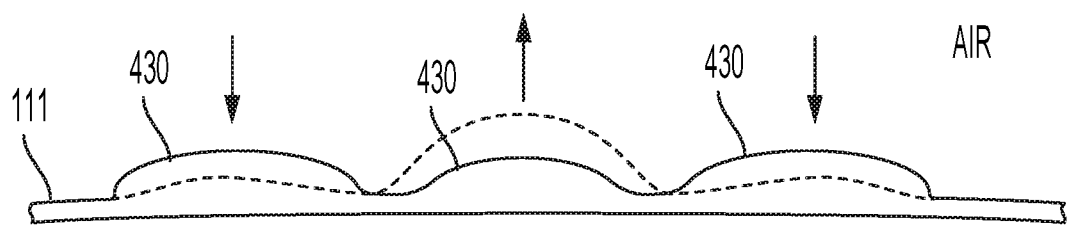
FIG. 43A illustrates a top view of bladders that may be integrated into a wearable device, according to an embodiment.
Figure 43B:
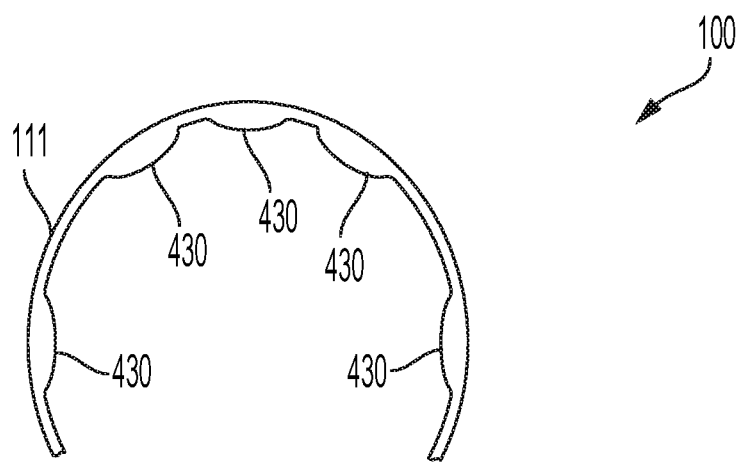
FIG. 43B illustrates the bladders in use with the wearable device, according to an embodiment.

FIG. 43A illustrates a top view of bladders 430 that may be integrated into body 111 of wearable device 100, as shown in FIG. 43B. Bladders 430 may retain gas or fluid, such as air. Bladders 430 may be used to conform wearable device 100 to different areas of the head of user 10. Adding air to certain areas may allow for better contact of electrodes or conductive sensors, such as bio-signal sensors 20, 22, on user 10. Bladders 430 may be controlled by a configuration of valves, and actuated by pressure on the bladder by user 10.

In some embodiments, expanding air in one bladder 430 may reduce air in another section or bladder 430.

In some embodiments, bladders 430 could pulsate to provide a massaging effect on user 10 as wearable device 100 is on the head of user 10.

In an aspect, the wearable device may used to obtain bio-signal data during sleep. For example, a baseline may be established for what is considered an "ideal" sleep. The user's bio-signals may be compared to the baseline to establish a sleep score based on the deviation of the signals from the baseline, such as a deviation of a signal amplitude or a time in which the signal amplitude meets a baseline threshold. In some embodiments, the bio-signal data is timestamped. In some embodiments, the bio-signal acquired during sleep may be used to improve the sleep of the user, for example, by providing a smart wakeup function, arousing the user when they are in a light sleep, or by training the user to sleep better (such as suggesting when a user should sleep based on drowsiness, focus, etc.).

Conveniently, electronics module 32 may be removable, as described herein, and in combination with a machine washable fabric 121 used for body 111, may allow for wearable device 100 to be machine washable upon removal of the electronics module 32.

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be understood by those skilled in the relevant arts, with respect to both processes and any systems, devices, etc., described herein, a wide range of variations is possible, and even advantageous, in various circumstances, without departing from the scope of the invention, which is to be limited only by the claims.

Of course, the above described embodiments are intended to be illustrative only and in no way limiting. The described embodiments are susceptible to many modifications of form, arrangement of parts, details and order of operation. The disclosure is intended to encompass all such modification within its scope, as defined by the claims.

What is claimed is:

1. A wearable device to wear on a head of a user, the device comprising:
a flexible band shaped to correspond to the user's head, the flexible band including a front portion configured to contact at least part of a frontal region of the user's head, a rear portion configured to contact at least part of an occipital region of the user's head, and at least one side portion extending between the front portion and the rear portion configured to contact at least part of a posterior auricular region of the user's head;
a flexible electroencephalography (EEG) bio-signal sensor disposed on the flexible band to receive EEG bio-signals from the user; and
a deformable above-ear electrode disposed in the at least one side portion of the flexible band, the deformable above-ear electrode comprising flexible conductive material as part of an additional bio-signal sensor configured to contact at least part of an upper and rear surface of an ear of the user, wherein the front portion and the rear portion are joined at the at least one side portion, and wherein when the wearable device is configured to be placed on the head of the user, downward pressure is distributed along the length of the flexible conductive material to contour the flexible conductive material to the upper and rear surface of the ear of the user and to collapse the flexible conductive material upwards;

wherein at least one portion of the flexible band includes an elastic substrate that elongates to a stretched state when worn; and wherein the flexible conductive material is formed from a conductive layer applied to a substrate.

2. The device of claim 1, wherein the flexible EEG bio-signal sensor is disposed on the front portion of the flexible band.

3. The device of claim 1, wherein the flexible EEG bio-signal sensor includes a flexible printed circuit board.

4. The device of claim 1, wherein the flexible EEG bio-signal sensor includes a silver ink conductive material configured to contact a forehead of the user.

5. The device of claim 1, further comprising:
a flexible luminescence array disposed on the front portion of the flexible band,
wherein the front portion is extendable to cover eyes of the user such that the flexible luminescence array is adjacent to the eyes of the user to provide light to the user.

6. The device of claim 1, wherein the flexible band includes a deformable fabric.

7. The device of claim 1, wherein the deformable above-ear electrode is configured to contact at least part of a mastoid bone region of the user.

8. The device of claim 1, wherein the flexible conductive material is a conductive rubber.

9. The device of claim 1, wherein the additional bio-signal sensor is an electrophysiological sensor.

10. The device of claim 1, further comprising an electronics module in communication with the flexible EEG bio-signal sensor for receiving the EEG bio-signals from the flexible EEG bio-signal sensor.

11. The device of claim 10, wherein the electronics module is disposed on the flexible band.

12. The device of claim 10, wherein the electronics module is selectively mountable to the flexible band.

13. The device of claim 10, wherein the electronics module includes a computing device configured to receive the EEG signals from the flexible EEG bio-signal sensor and to process the EEG bio-signals.

14. The device of claim 13, wherein the computing device is configured to process the EEG bio-signals to obtain bio-signal data during sleep.

15. The device of claim 14, wherein the computing device is configured to compare the bio-signal data to a baseline to establish a sleep score based on a deviation of the bio-signal data from the baseline.

16. The device of claim 1, further comprising a hair-penetrating sensor disposed on the flexible band.

17. The device of claim 1, further comprising an auxiliary sensor comprising at least one of an optical heart rate sensor, a pulse oximeter sensor, a gyroscope, an accelerometer, a magnetometer, a breath sensor, or a microphone.

18. The device of claim 1, further comprising an inner-ear sensor configured to contact an ear canal of the user.

19. The device of claim 18, further comprising a speaker disposed adjacent to the inner-ear sensor.

20. The device of claim 1 wherein:
the deformable above-ear electrode is disposed on a lower section of the side portion; and
the upper and rear surface of the ear of the user comprises a top of an auricular sulcus of the user.

21. The device of claim 1 wherein:
the deformable above-ear electrode is disposed on a lower section of the side portion; and
the upper and rear surface of the ear of the user comprises a region between an ear tip and the head of the user.

22. The device of claim 1, wherein the above-ear electrode comprises an open aperture in an inner region of the above-ear electrode and the flexible conductive material can collapse into the open aperture when worn.

23. The device of claim 1, wherein the above-ear electrode comprises a surface of compressible foam on which the flexible conductive material is disposed and the flexible conductive material can collapse into the surface of the compressible foam when worn.

* * * * *